United States Patent
Katz et al.

(10) Patent No.: US 12,094,224 B2
(45) Date of Patent: Sep. 17, 2024

(54) SYSTEM AND METHOD FOR DRIVER MONITORING

(71) Applicant: eyeSight Mobile Technologies Ltd., Herzliya (IL)

(72) Inventors: Itay Katz, Tel Aviv (IL); Yonatan Samet, Givataim (IL); Tamir Anavi, Kfar Yona (IL)

(73) Assignee: eyeSight Mobile Technologies Ltd., Herzliya (IL)

( * ) Notice: Subject to any disclaimer, the term of this patent is extended or adjusted under 35 U.S.C. 154(b) by 0 days.

(21) Appl. No.: 16/314,675

(22) PCT Filed: Jun. 30, 2017

(86) PCT No.: PCT/US2017/040378
§ 371 (c)(1),
(2) Date: Jan. 1, 2019

(87) PCT Pub. No.: WO2018/006019
PCT Pub. Date: Jan. 4, 2018

(65) Prior Publication Data
US 2019/0318181 A1 Oct. 17, 2019

Related U.S. Application Data

(60) Provisional application No. 62/357,902, filed on Jul. 1, 2016, provisional application No. 62/358,480, filed on Jul. 5, 2016.

(51) Int. Cl.
*G06V 20/59* (2022.01)
*B60K 28/02* (2006.01)
(Continued)

(52) U.S. Cl.
CPC ............ *G06V 20/597* (2022.01); *B60K 28/02* (2013.01); *B60W 40/09* (2013.01); *G06F 3/012* (2013.01);
(Continued)

(58) Field of Classification Search
CPC .......... G06K 9/00845; G06K 9/00597; B60K 28/02; G06F 3/013; G06F 3/011; G06F 3/017; G06F 3/012; G06F 3/913; A61B 5/163; A61B 3/0025; A61B 3/113; A61B 5/18; A61B 5/00; B60W 2540/00;
(Continued)

(56) References Cited

U.S. PATENT DOCUMENTS 6,989,754 B2 * 1/2006 Kisacanin ............. G01S 13/867
340/576
7,859,652 B2 * 12/2010 Uechi ................... B60W 30/10
356/29

(Continued)

*Primary Examiner* — Samir A Ahmed
(74) *Attorney, Agent, or Firm* — Bochner PLLC; Ariel Reinitz

(57) ABSTRACT

Systems and methods are disclosed for driver monitoring. In one implementation, one or more images are received, e.g., from an image sensor. Such image(s) can reflect a at least a portion of a face of a driver. Using the images, a direction of a gaze of the driver is determined. A set of determined (Continued)

driver gaze directions is identified using at least one predefined direction. One or more features of one or more eyes of the driver are extracted using information associated with the identified set.

20 Claims, 13 Drawing Sheets

(51) Int. Cl.
*B60W 40/09* (2012.01)
*G06F 3/01* (2006.01)
*G06V 40/18* (2022.01)
*B60W 40/08* (2012.01)

(52) U.S. Cl.
CPC ............ *G06F 3/013* (2013.01); *G06V 40/193* (2022.01); *B60W 2040/0818* (2013.01)

(58) Field of Classification Search
CPC ...... B60W 40/08; B60W 50/08; B60W 40/09; B60W 2040/0818; B62D 1/02; G06V 20/597; G06V 40/193; G06V 40/18
See application file for complete search history.

(56) References Cited

U.S. PATENT DOCUMENTS

| | | | |
|---|---|---|---|
| 8,538,044 B2* | 9/2013 | Tsukizawa | G06T 7/68 381/117 |
| 2004/0239509 A1* | 12/2004 | Kisacanin | A61B 5/18 340/575 |
| 2009/0237644 A1* | 9/2009 | Uechi | B60W 30/10 356/29 |
| 2011/0249868 A1* | 10/2011 | Tsukizawa | A61B 5/163 382/103 |
| 2014/0043459 A1* | 2/2014 | Tsukizawa | A61B 3/113 348/78 |
| 2014/0139655 A1* | 5/2014 | Mimar | G08B 21/0476 340/575 |
| 2014/0204193 A1* | 7/2014 | Zhang | G06K 9/00597 348/78 |
| 2015/0234459 A1* | 8/2015 | George-Svahn | B60K 35/00 345/156 |
| 2016/0085299 A1* | 3/2016 | Horesh | G06F 3/013 345/156 |
| 2016/0086338 A1* | 3/2016 | Nagamatsu | G02B 27/0093 348/78 |
| 2017/0039869 A1* | 2/2017 | Gleim | G09B 7/00 |

* cited by examiner

SYSTEM AND METHOD FOR DRIVER MONITORING

CROSS-REFERENCE TO RELATED APPLICATIONS

This application is related to and claims the benefit of priority to U.S. Patent Application No. 62/357,902, filed Jul. 1, 2016, and U.S. Patent Application No. 62/358,480, filed Jul. 5, 2016, each of which is incorporated herein by reference in its entirety.

TECHNICAL FIELD

Aspects and implementations of the present disclosure relate to data processing and, more specifically, but without limitation, to driver monitoring, driver gaze determination, determination of driver location and seat position, determination of driver behavior during driving, transmission of driver related data across a vehicle, and the combination of multiple sensors and vehicle information to analyze a driver in real-time and during periods of time.

BACKGROUND

In order to operate a motor vehicle safely, the driver of such vehicle must focus his/her attention on the road or path being traveled. Periodically, the attention of the driver may change (e.g., when looking at the mirrors of the vehicle). Various existing eye tracking systems can be configured to track a user's gaze. Such systems generally need to be calibrated in order to operate effectively.

SUMMARY

The following presents a shortened summary of various aspects of this disclosure in order to provide a basic understanding of such aspects. This summary is not an extensive overview of all contemplated aspects, and is intended to neither identify key or critical elements nor delineate the scope of such aspects. Its purpose is to present some concepts of this disclosure in a compact form as a prelude to the more detailed description that is presented later.

In one aspect of the present disclosure, systems and methods are disclosed for driver monitoring. In one implementation, one or more images are received, e.g., from an image sensor. Such image(s) can reflect a at least a portion of a face of a driver. Using the images, a direction of a gaze of the driver is determined. A set of determined driver gaze directions is identified using at least one predefined direction. One or more features of one or more eyes of the driver are extracted using information associated with the identified set.

BRIEF DESCRIPTION OF THE DRAWINGS

Aspects and implementations of the present disclosure will be understood more fully from the detailed description given below and from the accompanying drawings of various aspects and implementations of the disclosure, which, however, should not be taken to limit the disclosure to the specific aspects or implementations, but are for explanation and understanding only.

DETAILED DESCRIPTION

Aspects and implementations of the present disclosure are directed to driver gaze determination.

It can be appreciated that various eye-tracking techniques enable the determination of user gaze (e.g., the direction/location at which the eyes of a user are directed or focused). However, such techniques require that a correlation be identified/determined between the eye(s) of the user and another object. For example, in addition to a camera that perceives the eye(s) of the user, certain technologies utilize a second camera that is directed outwards (i.e., in the direction the user is looking). The images captured by the respective cameras (e.g., those reflecting the user gaze and those depicting the object at which the user is looking) then must be correlated. Alternatively, other solutions present the user with an icon, indicator, etc., at a known location/device. The user must then look at the referenced icon, at which point the calibration can be performed. However, both of the referenced solutions entail numerous shortcomings. For example, both solutions require additional hardware which may be expensive, difficult to install/configure, or otherwise infeasible.

Accordingly, described herein in various implementations are systems, methods, and related technologies for driver monitoring. As described herein, the disclosed technologies overcome the referenced shortcomings and provide numerous additional advantages and improvements. For example, the disclosed technologies can accurately compute the referenced determinations without the need for a second camera and without the need for the user/driver to look at a specific location/indicator at a certain moment in time.

It can therefore be appreciated that the described technologies are directed to and address specific technical challenges and longstanding deficiencies in multiple technical areas, including but not limited to image processing, eye tracking, and machine vision. As described in detail herein, the disclosed technologies provide specific, technical solutions to the referenced technical challenges and unmet needs in the referenced technical fields and provide numerous advantages and improvements upon conventional approaches. Additionally, in various implementations one or more of the hardware elements, components, etc., referenced herein operate to enable, improve, and/or enhance the described technologies, such as in a manner described herein.

Figure 1:
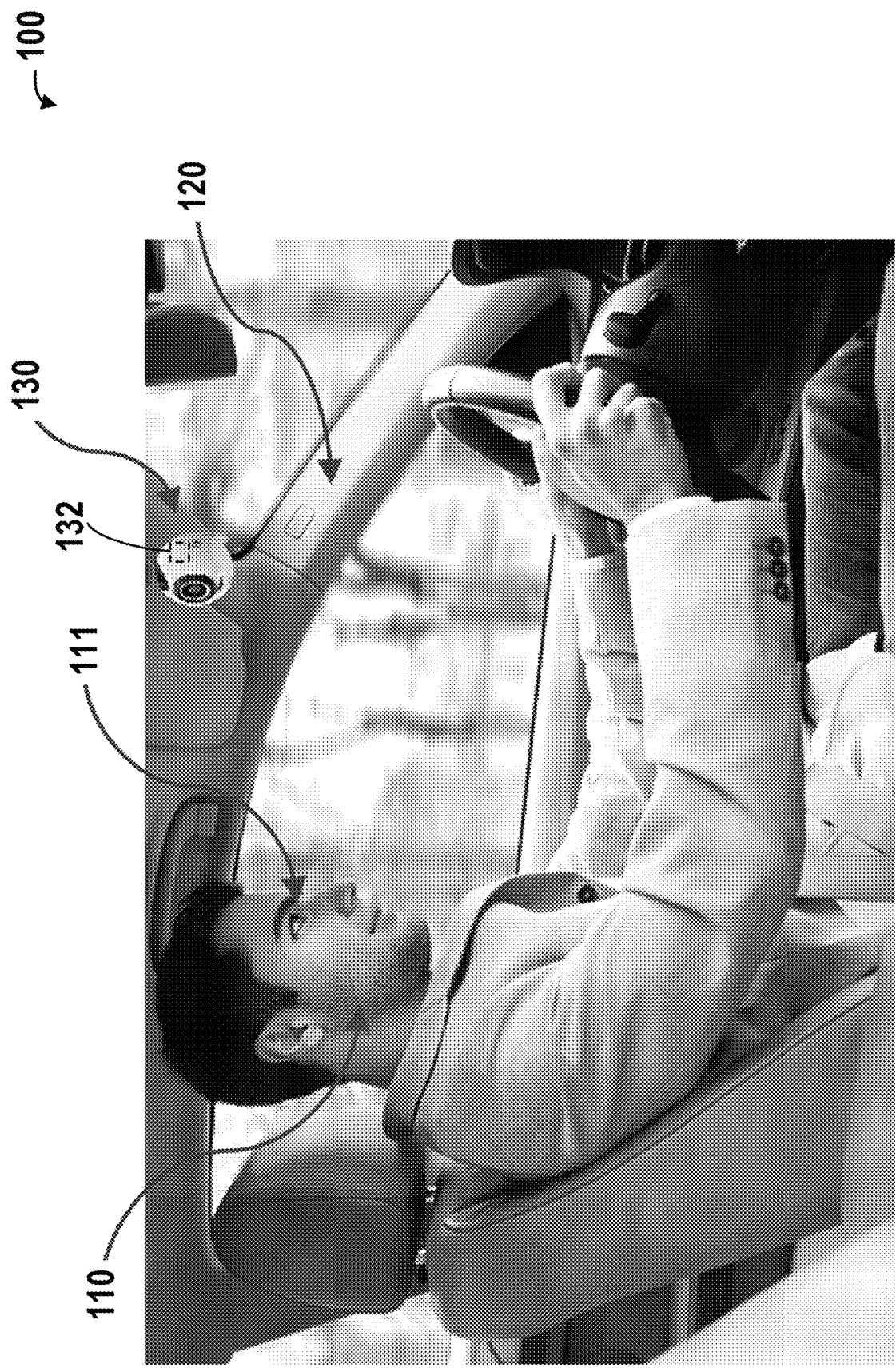
FIG. 1 illustrates an example system, in accordance with an example embodiment.

FIG. 1 illustrates an example system 100, in accordance with some implementations. As shown, the system 100 includes sensor 130 which can be an image acquisition device (e.g., a camera), image sensor, IR sensor, or any other such sensor described herein. Sensor 130 can be positioned or oriented within vehicle 120 (e.g., a car, bus, or any other such vehicle used for transportation). In certain implementations, sensor 130 can include or otherwise integrate one or more processor(s) 132 that process image(s) and/or other such content captured by the sensor. In other implementations, sensor 130 can be configured to connect and/or otherwise communicate with other device(s) (as described herein), and such devices can receive and process the referenced image(s).

Sensor 130 (e.g., a camera) may include, for example, a CCD image sensor, a CMOS image sensor, a light sensor, an IR sensor, an ultrasonic sensor, a proximity sensor, a short-wave infrared (SWIR) image sensor, a reflectivity sensor, an RGB camera, a black and white camera, or any other device that is capable of sensing visual characteristics of an environment. Moreover, sensor 130 may include, for example, a single photosensor or 1-D line sensor capable of scanning an area, a 2-D sensor, or a stereoscopic sensor that includes, for example, a plurality of 2-D image sensors. In certain implementations, a camera, for example, may be associated with a lens for focusing a particular area of light onto an image sensor. The lens can be narrow or wide. A wide lens may be used to get a wide field-of-view, but this may require a high-resolution sensor to get a good recognition distance. Alternatively, two sensors may be used with narrower lenses that have an overlapping field of view; together, they provide a wide field of view, but the cost of two such sensors may be lower than a high-resolution sensor and a wide lens.

Sensor 130 may view or perceive, for example, a conical or pyramidal volume of space. Sensor 130 may have a fixed position (e.g., within vehicle 120). Images captured by sensor 130 may be digitized and input to the at least one processor 132, or may be input to the at least one processor 132 in analog form and digitized by the at least one processor.

It should be noted that sensor 130 as depicted in FIG. 1, as well as the various other sensors depicted in other figures and described and/or referenced herein may include, for example, an image sensor configured to obtain images of a three-dimensional (3-D) viewing space. The image sensor may include any image acquisition device including, for example, one or more of a camera, a light sensor, an infrared (IR) sensor, an ultrasonic sensor, a proximity sensor, a CMOS image sensor, a shortwave infrared (SWIR) image sensor, or a reflectivity sensor, a single photosensor or 1-D line sensor capable of scanning an area, a CCD image sensor, a reflectivity sensor, a depth video system comprising a 3-D image sensor or two or more two-dimensional (2-D) stereoscopic image sensors, and any other device that is capable of sensing visual characteristics of an environment. A user or other element situated in the viewing space of the sensor(s) may appear in images obtained by the sensor(s). The sensor(s) may output 2-D or 3-D monochrome, color, or IR video to a processing unit, which may be integrated with the sensor(s) or connected to the sensor(s) by a wired or wireless communication channel.

Figure 12:
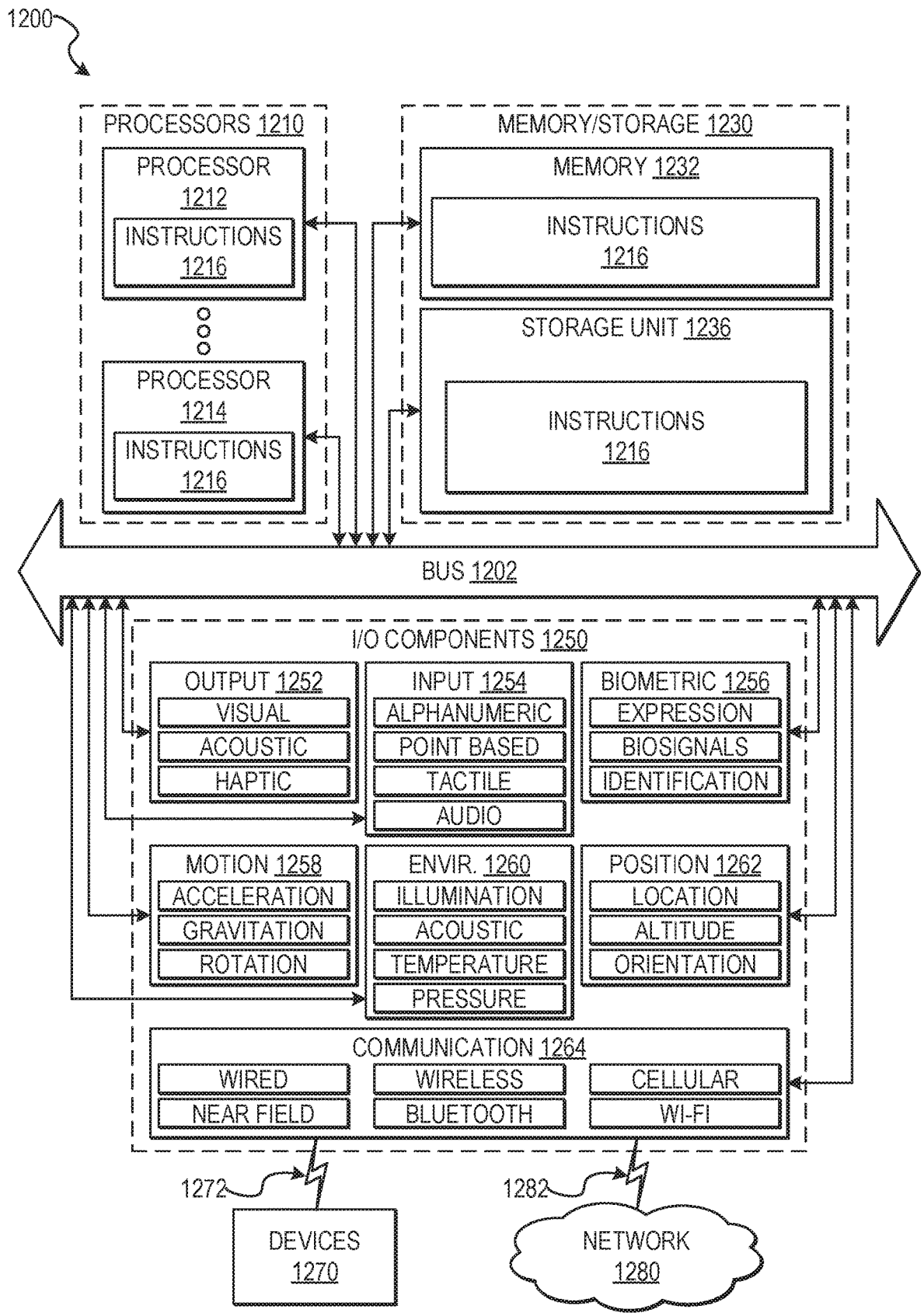
FIG. 12 is a block diagram illustrating components of a machine able to read instructions from a machine-readable medium and perform any of the methodologies discussed herein, according to an example embodiment.

The at least one processor 132 as depicted in FIG. 1, as well as the various other processor(s) depicted in other figures and described and/or referenced herein may include, for example, an electric circuit that performs a logic operation on an input or inputs. For example, such a processor may include one or more integrated circuits, microchips, microcontrollers, microprocessors, all or part of a central processing unit (CPU), graphics processing unit (GPU), digital signal processors (DSP), field-programmable gate array (FPGA), an application-specific integrated circuit (ASIC), or any other circuit suitable for executing instructions or performing logic operations. The at least one processor may be coincident with or may constitute any part of a processing unit such as a processing unit which may include, among other things, a processor and memory that may be used for storing images obtained by the image sensor. The processing unit may include, among other things, a processor and memory that may be used for storing images obtained by the sensor(s). The processing unit and/or the processor may be configured to execute one or more instructions that reside in the processor and/or the memory. Such a memory (e.g., memory 1230 as shown in FIG. 12) may include, for example, persistent memory, ROM, EEPROM, EAROM, SRAM, DRAM, DDR SDRAM, flash memory devices, magnetic disks, magneto optical disks, CD-ROM, DVD-ROM, Blu-ray, and the like, and may contain instructions (i.e., software or firmware) or other data. Generally, the at least one processor may receive instructions and data stored by memory. Thus, in some embodiments, the at least one processor executes the software or firmware to perform functions by operating on input data and generating output. However, the at least one processor may also be, for example, dedicated hardware or an application-specific integrated circuit (ASIC) that performs processes by operating on input data and generating output. The at least one processor may be any combination of dedicated hardware, one or more ASICs, one or more general purpose processors, one or more DSPs, one or more GPUs, or one or more other processors capable of processing digital information.

Images captured by sensor 130 may be digitized by sensor 130 and input to processor 132, or may be input to processor 132 in analog form and digitized by processor 132. Example proximity sensors may include, among other things, one or more of a capacitive sensor, a capacitive displacement sensor, a laser rangefinder, a sensor that uses time-of-flight (TOF) technology, an IR sensor, a sensor that detects magnetic distortion, or any other sensor that is capable of generating information indicative of the presence of an object in proximity to the proximity sensor. In some embodiments, the information generated by a proximity sensor may include a distance of the object to the proximity sensor. A proximity sensor may be a single sensor or may be a set of sensors. Although a single sensor 130 is illustrated in FIG. 1, system 100 may include multiple types of sensors and/or multiple sensors of the same type. For example, multiple sensors may be disposed within a single device such as a data input device housing some or all components of system 100, in a single device external to other components of system 100, or in various other configurations having at least one external sensor and at least one sensor built into another component (e.g., processor 132 or a display) of system 100.

Processor 132 may be connected to or integrated within sensor 130 via one or more wired or wireless communication links, and may receive data from sensor 130 such as images, or any data capable of being collected by sensor 130, such as is described herein. Such sensor data can include, for example, sensor data of a user's head, eyes, face, etc. Images may include one or more of an analog image captured by sensor 130, a digital image captured or determined by sensor 130, a subset of the digital or analog image captured by sensor 130, digital information further processed by processor 132, a mathematical representation or transformation of information associated with data sensed by sensor 130, information presented as visual information such as frequency data representing the image, conceptual information such as presence of objects in the field of view of the sensor, etc. Images may also include information indicative the state of the sensor and or its parameters during capturing images e.g. exposure, frame rate, resolution of the image, color bit resolution, depth resolution, field of view of sensor 130, including information from other sensor(s) during the capturing of an image, e.g. proximity sensor information, acceleration sensor (e.g., accelerometer) information, information describing further processing that took place further to capture the image, illumination condition during capturing images, features extracted from a digital image by sensor 130, or any other information associated with sensor data sensed by sensor 130. Moreover, the referenced images may include information associated with static images, motion images (i.e., video), or any other visual-based data. In certain implementations, sensor data received from one or more sensor(s) 130 may include motion data, GPS location coordinates and/or direction vectors, eye gaze information, sound data, and any data types measurable by various sensor types. Additionally, in certain implementations, sensor data may include metrics obtained by analyzing combinations of data from two or more sensors.

In certain implementations, processor 132 may receive data from a plurality of sensors via one or more wired or wireless communication links. In certain implementations, processor 132 may also be connected to a display, and may send instructions to the display for displaying one or more images, such as those described and/or referenced herein. It should be understood that in various implementations the described, sensor(s), processor(s), and display(s) may be incorporated within a single device, or distributed across multiple devices having various combinations of the sensor(s), processor(s), and display(s).

As noted above, in certain implementations, in order to reduce data transfer from the sensor to an embedded device motherboard, processor, application processor, GPU, a processor controlled by the application processor, or any other processor, the system may be partially or completely integrated into the sensor. In the case where only partial integration to the sensor, ISP or sensor module takes place, image preprocessing, which extracts an object's features (e.g., related to a predefined object), may be integrated as part of the sensor, ISP or sensor module. A mathematical representation of the video/image and/or the object's features may be transferred for further processing on an external CPU via dedicated wire connection or bus. In the case that the whole system is integrated into the sensor, ISP or sensor module, a message or command (including, for example, the messages and commands referenced herein) may be sent to an external CPU. Moreover, in some embodiments, if the system incorporates a stereoscopic image sensor, a depth map of the environment may be created by image preprocessing of the video/image in the 2D image sensors or image sensor ISPs and the mathematical representation of the video/image, object's features, and/or other reduced information may be further processed in an external CPU.

As shown in FIG. 1, sensor 130 can be positioned to capture or otherwise receive image(s) or other such inputs of user 110 (e.g., a human user who may be the driver or operator of vehicle 120). Such image(s) can be captured in different frame rates (FPS)). As described herein, such image(s) can reflect, for example, various aspects of the face of user 110, including but not limited to the gaze or direction of eye(s) 111 of user 110, the position (location in space) and orientation of the face of user 110, etc. In one example, the system can be configured to capture the images in different exposure rates for detecting the user gaze. In another example, the system can alter or adjust the FPS of the captured images for detecting the user gaze. In another example, the system can alter or adjust the exposure and/or frame rate in relation to detecting the user wearing glasses and/or the type of glasses (sight glasses, sunglasses, etc.).

It should be understood that the scenario depicted in FIG. 1 is provided by way of example.

Accordingly, the described technologies can also be configured or implemented in various other arrangements, configurations, etc. For example, sensor 130 can be positioned or located in any number of other locations (e.g., within vehicle 120). For example, in certain implementations sensor 130 can be located above user 110, in front of the user 110 (e.g., positioned on or integrated within the dashboard of vehicle 110), to the side to of user 110 (such that the eye of the user is visible/viewable to the sensor from the side, which can be advantageous and overcome challenges caused by users who wear glasses), and in any number of other positions/locations. Additionally, in certain implementations the described technologies can be implemented using multiple sensors (which may be arranged in different locations).

In certain implementations, images, videos, and/or other inputs can be captured/received at sensor 130 and processed (e.g., using face detection techniques) to detect the presence of eye(s) 111 of user 110. Upon detecting the eye(s) of the user, the gaze of the user can be determined. In certain implementations, the gaze of the user can be determined using information such as the position of sensor 130 within vehicle 120. In other implementations, the gaze of the user can be further determined using additional information such as the location of the face of user 110 within the vehicle (which may vary based on the height of the user), user age, gender, face structure, inputs from other sensors including camera(s) positioned in different places in the vehicle, sensors that provide 3D information of the face of the user (such as TOF sensors), IR sensors, physical sensors (such as a pressure sensor located within a seat of a vehicle), proximity sensor, etc. In other implementations, the gaze or gaze direction of the user can be identified, determined, or extracted by other devices, systems, etc. and transmitted/provided to the described system. Upon detecting/determining the gaze of the user, various features of eye(s) 111 of user 110 can be further extracted, as described herein.

It should be understood that the 'gaze of a user,' 'eye gaze,' etc., as described and/or referenced herein, can refer to the manner in which the eye(s) of a human user are positioned/focused. For example, the 'gaze' or 'eye gaze' of user 110 can refer to the direction towards which eye(s) 111 of user 110 are directed or focused e.g., at a particular instance and/or over a period of time. By way of further example, the 'gaze of a user' can be or refer to the location the user looks at a particular moment. By way of yet further example, the 'gaze of a user' can be or refer to the direction the user looks at a particular moment.

Moreover, in certain implementations the described technologies can determine/extract the referenced gaze of a user using various techniques such as those known to those of ordinary skill in the art. For example, in certain implementations a sensor (e.g., an image sensor, camera, IR camera, etc.) may capture image(s) of eye(s) (e.g., one or both human eyes). Such image(s) can then be processed, e.g., to extract various features such as the pupil contour of the eye, reflections of the IR sources (e.g., glints), etc. The gaze or gaze vector(s) can then be computed/output, indicating the eyes' gaze points (which can correspond to a particular direction, location, object, etc.).

Additionally, in certain implementations the described technologies can compute, determine, etc., that gaze of the user is directed towards (or is likely to be directed towards) a particular item, object, etc., e.g., under certain circumstances. For example, as described herein, in a scenario in which a user is determined to be driving straight on a highway, it can be determined that the gaze of user 110 as shown in FIG. 1 is directed towards (or is likely to be directed towards) the road ahead/horizon. It should be understood that 'looking towards the road ahead' as referenced here can refer to a user such as a driver of a vehicle whose gaze/focus is directed/aligned towards the road/path visible through the front windshield of the vehicle being driven (when driving in a forward direction).

In some implementations, processor 132 is configured to initiate various action(s), such as those associated with aspects, characteristics, phenomena, etc. identified within captured or received images. The action performed by the processor may be, for example, generation of a message or execution of a command (which may be associated with detected aspect, characteristic, phenomenon, etc.). For example, the generated message or command may be addressed to any type of destination including, but not limited to, an operating system, one or more services, one or more applications, one or more devices, one or more remote applications, one or more remote services, or one or more remote devices.

It should be noted that, as used herein, a 'command' and/or 'message' can refer to instructions and/or content directed to and/or capable of being received/processed by any type of destination including, but not limited to, one or more of: operating system, one or more services, one or more applications, one or more devices, one or more remote applications, one or more remote services, or one or more remote devices.

It should also be understood that the various components referenced herein can be combined together or separated into further components, according to a particular implementation. Additionally, in some implementations, various components may run or be embodied on separate machines. Moreover, some operations of certain of the components are described and illustrated in more detail herein.

The presently disclosed subject matter can also be configured to enable communication with an external device or website, such as in response to a selection of a graphical (or other) element. Such communication can include sending a message to an application running on the external device, a service running on the external device, an operating system running on the external device, a process running on the external device, one or more applications running on a processor of the external device, a software program running in the background of the external device, or to one or more services running on the external device. Additionally, in certain implementations a message can be sent to an application running on the device, a service running on the device, an operating system running on the device, a process running on the device, one or more applications running on a processor of the device, a software program running in the background of the device, or to one or more services running on the device.

"Image information," as used herein, may be one or more of an analog image captured by sensor 130, a digital image captured or determined by sensor 130, subset of the digital or analog image captured by sensor 130, digital information further processed by an ISP, a mathematical representation or transformation of information associated with data sensed by sensor 130, frequencies in the image captured by sensor 130, conceptual information such as presence of objects in the field of view of sensor 130, information indicative of the state of the image sensor or its parameters when capturing an image (e.g., exposure, frame rate, resolution of the image, color bit resolution, depth resolution, or field of view of the image sensor), information from other sensors when sensor 130 is capturing an image (e.g. proximity sensor information, or accelerometer information), information describing further processing that took place after an image was captured, illumination conditions when an image is captured, features extracted from a digital image by sensor 130, or any other information associated with data sensed by sensor 130. Moreover, "image information" may include information associated with static images, motion images (i.e., video), or any other visual-based data.

Figure 2:
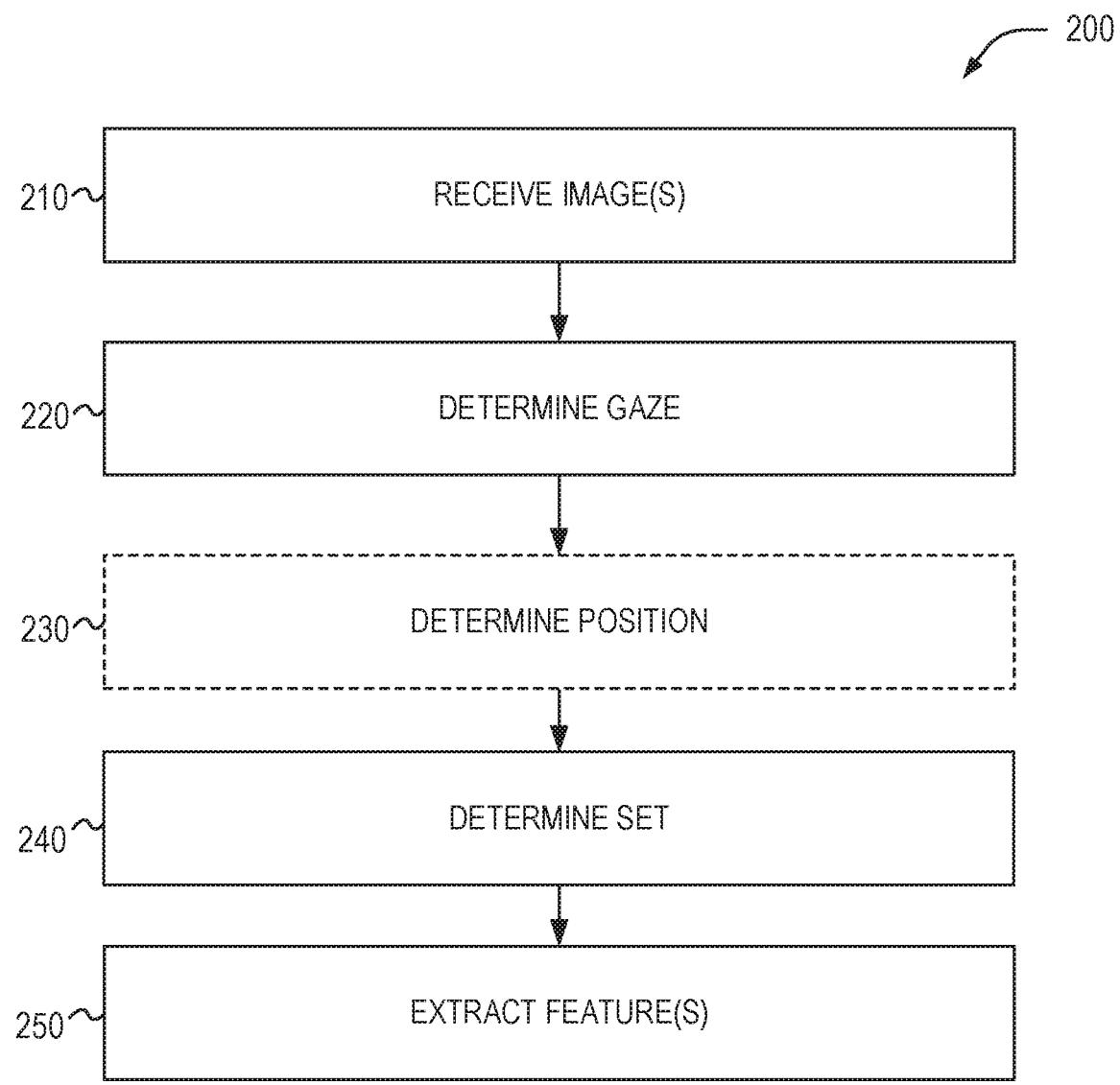
FIG. 2 is a flow chart illustrating a method, in accordance with an example embodiment, for driver monitoring.

FIG. 2 is a flow chart illustrating a method 200, according to an example embodiment, for driver gaze determination. The method is performed by processing logic that can comprise hardware (circuitry, dedicated logic, etc.), software (such as is run on a computing device such as those described herein), or a combination of both. In one implementation, the method 200 (and the other methods described herein) is/are performed by one or more elements depicted and/or described in relation to FIG. 1 (including but not limited to device sensor 130 and/or integrated/connected computing devices, as described herein). In some other implementations, the one or more blocks of FIG. 2 can be performed by another machine or machines.

For simplicity of explanation, methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term article of manufacture, as used herein, is intended to encompass a computer program accessible from any computer-readable device or storage media.

At operation 210, one or more images are received. In certain implementations, such image(s) can be captured at and/or received from a sensor such as an image sensor (e.g., sensor 130 as depicted in FIG. 1). As noted above, such image(s) can include and/or otherwise reflect a face of user (and/or a portion thereof). For example, as shown in FIG. 1, sensor 130 can be oriented to capture image(s) of eyes 111 of user 110 (here, a driver of vehicle 120).

At operation 220, a direction of a gaze of the user is determined. In certain implementations, the direction of the referenced gaze can be determined using image(s) captured by a sensor (e.g., the image(s) captured/received at operation 210). For example, as shown in FIG. 1, image(s) captured by sensor 130 can be processed or otherwise analyzed to determine the direction of the gaze of user 110.

In certain implementations, the direction of the gaze of the user can reflect a location at which the user is looking, e.g., at a particular time. For example, in a scenario in which the eye(s) of the driver are looking at the road ahead (e.g., through the front windshield of the vehicle which he/she is driving), the gaze of such a user can be determined to be directed straight, towards the road ahead, etc.

Figure 3A:
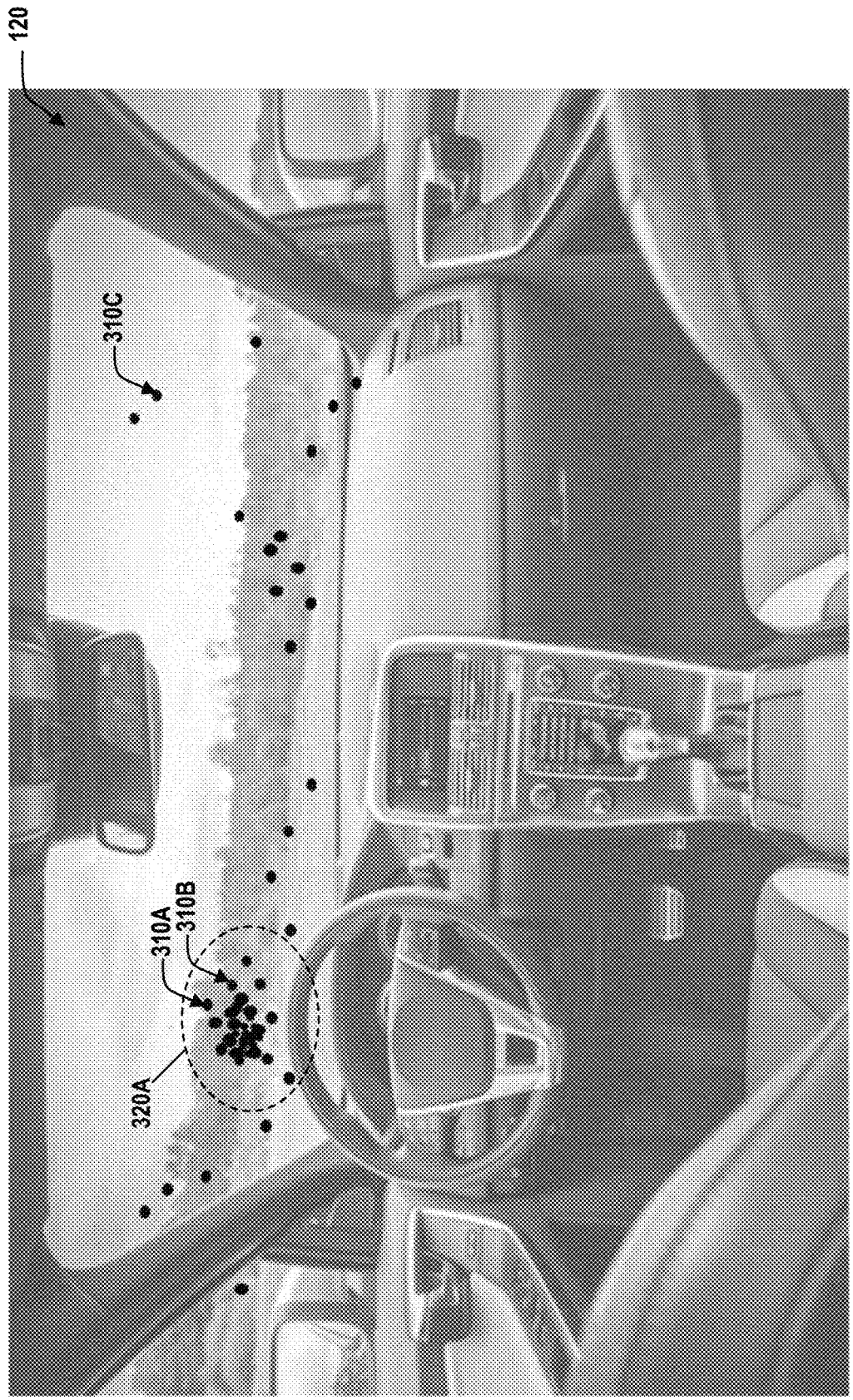
FIG. 3A illustrates an example scenario described herein, according to an example embodiment.
Figure 3B:
FIG. 3B illustrates an example scenario described herein, according to an example embodiment.

By way of illustration, FIG. 3A depicts various dots or points 310 plotted with respect to vehicle 120. Each of the depicted points represents a recognized direction of the gaze of the driver of vehicle 120, e.g., at a particular moment in time. For example, points 310A, 310B, and 310C correspond to locations that the gaze of the user was directed to (e.g., at different moments in time). Another example scenario is depicted in FIG. 3B. As shown in FIG. 3B, the gaze of the user can be directed to various locations inside vehicle 120 (e.g., points 310E and 310F) and/or outside vehicle 120 (e.g., point 310D).

At operation 230, a position, orientations, etc. of the head/face of the user/driver is determined. In certain implementations, such a position/orientation can be determined using the images(s) captured by sensor 130 (e.g., using face/head detection and/or other such image processing techniques as are well known in the art). It should be understood that the position/orientation of the head/face of the user may be determined in certain scenarios but not determined (or not necessarily determined) in other scenarios. For example, in a scenario in which the user looks is looking straight/forward (and/or towards a far distance), the position of the head may not necessarily be determined. In other scenarios (e.g., when the user is looking towards a close distance, e.g., at an object/location within the vehicle, at the side mirrors of the vehicle, etc.) the position and orientation of the head can be determined, e.g., in order to extract and calibrate the features of the eyes of the user (when the user is looking towards close distances, as noted). It should also be noted that in certain implementations the system may receive the position and/or orientation of the user's face/head from another system, device, source, etc.

At operation 240, a set of determined driver gaze directions is identified. In certain implementations, such a set can be identified using one or more predefined direction(s)/in relation to such predefined direction(s). Such a predefined direction can reflect, for example, a direction that is aligned or consistent with the direction of the motion of the vehicle within which the driver is present is traveling (e.g., a straight/forward direction). Accordingly, such a predefined direction can define the manner in which the eye gaze of a user is expected to be/is likely to be directed, e.g., under certain circumstances. For example, when traveling straight on a highway, the eye gaze of a user is expected to be directed towards a location that is straight/towards the road ahead. In certain implementations, various recognized driver gaze direction(s) can be correlated with the referenced predefined direction. It should be understood that the referenced predefined direction(s) are provided by way of example and that other predefined direction(s) (e.g., the direction of a mirror of the vehicle, the direction of an in-vehicle navigation system, etc.) can also be utilized in a comparable manner.

By way of illustration, FIG. 3A depicts set 320A which includes points 310A and 310B and reflects those instances during which the gaze of the driver was directed towards a particular location (here, straight, towards the road ahead). As shown in FIG. 3A, point 310C (corresponding to a moment at which the gaze of the user was directed to another location, e.g., the sky) is not included in set 320A. By identifying those driver gaze directions that correspond to the referenced predefined direction (e.g., the direction(s) of points 310A and 310B which correspond to a driver looking straight ahead), can be further utilized to extract various feature(s) of the eyes of the driver, e.g., as described herein.

In certain implementations, the system can recognize a set of different gaze directions along window of time, e.g., a set that has a high probability to reflect the gaze of the user to a predefined location. For example, a set that is high probability in reflecting a driver gaze when looking straight ahead. Once the set is identified, the driver eye features are extracted, e.g., using the data associated with that set. In one example, within this set, the system selects part of the set to reflect the gaze of the driver toward the predefined location (e.g., looking forward), and filters out other samples of gaze direction (relating to them as "noise"). In certain implementations, different methods can be utilized for selecting the set of gaze-direction within the original determined set (e.g. 320A). In one example, a median filter can be used on the determined set (e.g. 320A). In another example, the sampled gaze-directions in the determined set can be averaged. In yet another example, a probability distribution graph of the gaze-direction can be created and the set of gaze-direction can be selected according to the volume of distribution of the samples gaze-direction.

In certain implementations, such a set of determined driver gaze directions can be identified using information (e.g., a priori information) associated with the distribution of the driver gaze during driving (e.g., the distribution of driver gaze inside/outside the car during driving, etc.). For example, it can be defined and/or determined that the gaze of the driver is expected to be directed towards the road ahead a defined percentage of the time (e.g., at least 80% of the time when the driver is driving straight on a highway). Accordingly, upon receiving information or otherwise determining that the vehicle is traveling straight and/or located on a highway, it can be determined that the gaze of the user is expected to be/likely to be directed straight towards the road ahead.

By way of further illustration, when a user is driving at high speeds, and while the steering wheel of the vehicle is straight, the distribution of the driver's gaze is centered at the road's vanishing point (e.g., in both horizontal and vertical components). Accordingly, in such a scenario the described system can use a default set of eye parameters, and collect the computed driver's gaze points (e.g., over several thousands of frames/images). The system can then identify/find/determine which frame(s) correspond to the driver's gaze being directed towards the vanishing point. This may be done by computing/finding the median value of the calculated gaze points, or by finding the mean of the distribution of gaze points. In certain implementations, some of the eye parameters/features can be corrected, e.g., so that the gaze calculated on these frames will be equal to the vanishing point. For example, this may be done by changing the Kappa angle parameters (horizontal and vertical). It should be understood that 'eye parameters' or 'features' (as referenced herein) can refer to various physical parameters (and/or a set thereof), such as those which can be used to compute gaze direction from image-based features. These parameters may include physical parameters describing the eye, and/or regression coefficients for this computation. The new eye parameters can then be applied to gaze calculations, e.g., from here on.

In other implementations, such a set of determined driver gaze directions can be identified using information (e.g., a priori information) associated with the distribution of driver gaze based on various driving behaviors (and/or other aspect of the operation of the vehicle). That is, as described herein, it can be appreciated that various driving behaviors (e.g., turning, activating turn signals, etc.) can indicate that the gaze of the driver is likely directed in a particular direction. For example, it can be defined and/or determined that the gaze of the driver may be affected by various phenomena such as speed or maneuvering of the vehicle, location of the vehicle, looking in mirrors etc. Accordingly, such factors (e.g., as determined by one or more sensors integrated within the vehicle and/or another device) can be accounted for in determining the referenced driver gaze direction.

In yet other implementations, such a set of determined driver gaze directions can be identified using information (e.g., a priori information) associated with the distribution of the driver gaze based on actions taken/performed by the driver (e.g., within the vehicle and/or in relation to components of the vehicle. For example, it can be appreciated that certain behaviors (e.g., looking at mirrors, looking at an in-vehicle navigation system, looking at a passenger, etc.) may affect or alter the gaze of the driver. Accordingly, such factors can be accounted for in determining the referenced driver gaze direction. Moreover, in certain implementations the position of various objects (e.g., mirrors) within a vehicle can be accounted for in identifying the set of determined driver gaze directions.

In certain implementations, multiple sets of driver gaze directions can be determined (e.g., a first set of driver gaze directions, a second set of driver gaze directions, etc.). For example, in addition to set 320A (as depicted in FIG. 3A, reflecting driver gaze directions corresponding to the driver looking straight), FIG. 3B depicts set 320B of driver gaze directions corresponding to the driver looking at the left side mirror of vehicle 120.

In certain implementations, the referenced set of determined driver gaze directions can be identified using the position of the head of the driver (e.g., as determined at operation 230 and/or received from another device/source). For example, the position of the head of the driver can be accounted for in determining that the gaze of the driver is directed towards an object, element, etc., within the vehicle (e.g., an in-vehicle navigation system, a main mirror of a vehicle, a location on a touch screen device that the driver clicks on/selects) or outside the vehicle (e.g. the vehicle's side mirrors).

By way of illustration, the system can recognize the time a user clicked on/selected an icon (or other element) on a touch screen, e.g., by detecting the selected icon or receiving information from another system (e.g., an infotainment system in the car). Such information can reflect the user touching/clicking on a location on the touch screen associated with a specific icon, the location of the icon on the display and a time-stamp in which such selection took place. Based on the assumption that when a user is clicking on a specific location on a touch screen, at that moment the user is looking at that location (e.g., in order to point his finger toward that location on the touch screen), the system can use the: location of the icon within the space of the car, the location and orientation of the user's head/eyes, and the detected gaze-direction at that moment of touching/clicking on the icon, to extract features of the user's eye(s).

By way of further illustration, it can be appreciated that, inside a vehicle interior there various objects which a user may look at often (e.g. mirrors, infotainment system buttons/touch buttons, etc.). These objects have a fixed [x, y, z,] position relative to the sensor camera. The described system can utilize such information in various ways. For example, in one implementation the system can analyze 'hot spots' of the driver's calculated gaze (e.g., areas that the driver frequently looks at), and determine correspondences between calculated gaze points and objects (e.g., within the interior/cabin of the vehicle). In another implementation, the system analyzes 'hot spots' of the driver's calculated gaze, and correlates them with the driver's activity (e.g., lane changing, touching buttons, etc.) in order to determine correspondences between calculated gaze points and real objects in the cabin and/or behaviors of the driver. In each relevant frame, each eye's [x,y,z,] location is computed relative to the camera/sensor. This can be done by using 3D information of the drivers' face, and/or by using the distances between corneal reflections from different illumination sources at known positions. For each eye, a set of correspondences can be established, where each correspondence is between the physical position of the object, the position of the eye, and image-based features from that frame. Some of the eye parameters can be corrected, e.g., so that the gaze calculated for each such correspondence matches the gaze predicted by the relative object-eye-camera positions. It should be understood that eye parameters as referenced herein refers to a set of physical parameters which can be used in order to compute gaze direction from image based features. These parameters can include physical parameters describing the eye, or regression coefficients for this computation. The new eye parameters can then be applied to gaze calculations from here on.

At operation 250, one or more features of one or more eyes of the driver are extracted. Such features, eye features, features of eye(s) of a user, etc., can be, for example, various anatomical characteristics, parameters, etc. such as those that can be used for eye tracking and/or in other contexts. In certain implementations, such feature(s) are extracted using information associated with the identified set of determined driver gaze directions (e.g., as identified at operation 240). One example feature that can be extracted is a kappa angle of one or more eyes of the driver. Such a kappa angle can correspond to the angle between the pupillary axis and the visual axis of an eye of the user. Other example features that can be extracted include but are not limited to a radius of curvature of a cornea of an eye of the driver, and a distance between the pupil plane and a center of curvature of the cornea of an eye of the driver. It should be understood that such features are provided by way of example and that any number of other such features (e.g., anatomical parameters or characteristics of eye(s) of the user) can also be extracted.

Figure 4:
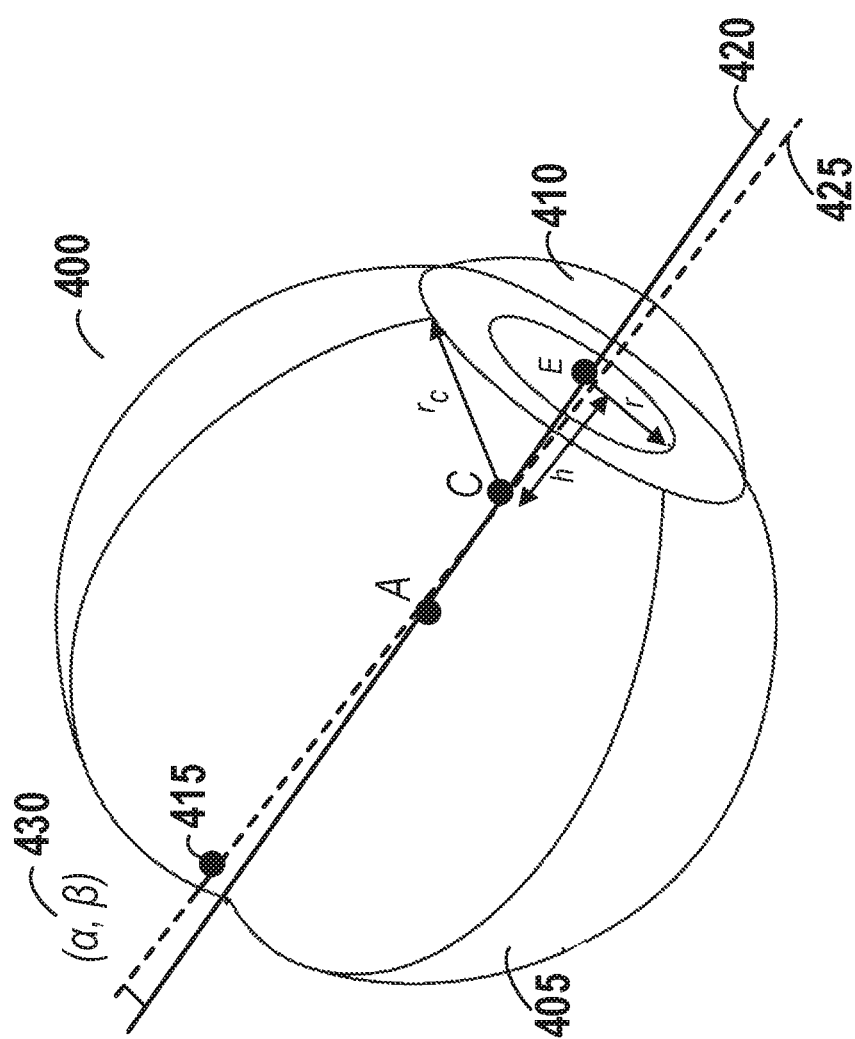
FIG. 4 illustrates an eye of a user, according to an example embodiment.

By way of further illustration, FIG. 4 depicts an example eye 400, such as is described herein. FIG. 4 depicts the proper locations of eyeball 405 and cornea 410 which may then be used to determine fovea 415 and optical axis 420. Fovea 415 and optical axis 420 may then be used to compute/determine visual axis 425 and kappa angle 430, e.g., as described herein.

For example, as referenced above, data relating to various image features of the image of the eye can be extracted, e.g., for further processing. This extracted data may be processed and then used to compute or obtain a gaze vector (e.g., associated with each eye). Such extracted data may include, for example: highly accurate location of glints, pupils, etc.

In certain implementations, processing of such image(s) and the determination of a gaze of a user, gaze vectors, etc., may be achieved via various operations. Such operations can include, for example: estimating an optical axis of the eye in the image, such as optical axis 420 of eye 400 of FIG. 4. Such an optical axis refers to a line that passes through the center of curvature of the cornea 410 and runs parallel to the axis of symmetry. It should be understood that eye 400 may contain cornea 410 and a lens (which may be used for focus), where reflection may be obtained from cornea 410. Additionally, a spherical mirror can be regarded as a model (e.g., a mathematical model) of cornea 410 (e.g., as opposed to a physical feature of eye 400). As described herein, various parameters of the optical axis can be computed based on one or more of image features, the radius of curvature of the cornea, and the distance of the cornea center of curvature and the pupil plane. Additionally, in certain implementations the referenced operations can further include estimating a visual axis of the eye in the image (e.g., visual axis 425 of eye 400 of FIG. 4, where the visual axis refers to a line that passes through the center of vision, such as through fovea 415 of FIG. 4, and the (optical) nodal point of the eye).

As also shown in FIG. 4, visual axis 425 may divert from optical axis 420 by an angle which is known as kappa ("κ") 430, where κ may include two components, such as a horizontal angle α (alpha) and a lateral angle β (beta). For example, average values for α may be 5° and for β may be 1.5°. Angle κ may be different for each person, such as from person to person, as well as being different for each eye, such as the left and the right eye. Further, κ may be measured for each individual by a calibration process.

In certain implementations, the visual axis may be obtained based on the optical axis by computing κ and the three-axes pose of the eye. Similarly, the pitch and yaw angles of the eye may also be obtained or known from the optical axis, while the roll angle may be obtained from one or more empirical laws, such as (without limitation) Donders' law (that the orientation of the eye when looking in a specific direction is always the same), Listing's law (that the axis of rotation of the eye lies in a common plane and the plane is perpendicular to the optical axis), etc.

Further, in certain implementations, having estimated the visual axis for one or both eye(s) (e.g., as described above), the visual axis along with the eye's optical axis (as well as other features) may then be used to compute or determine the gaze of a user. The gaze of the user may be used for accurate tracking of eyes which may then be used for any number of commercial and non-commercial software programs or applications. It is contemplated that an accurate eye tracking may facilitate a better and more accurate performance from any software application employing the eye tracking.

In certain implementations, respective feature(s) can be extracted from various determined driver gaze directions (e.g., those included within a set, such as a set of determined driver gaze directions identified at operation 240). For example, a first feature can be extracted with respect to a first determined driver gaze direction (e.g., point 310A as shown in FIG. 3A) and a second feature can be extracted with respect to a second determined driver gaze direction (e.g., point 310B).

Additionally, as noted above, in certain implementations multiple sets of determined driver gaze directions can be identified. Accordingly, in such scenarios, one feature can, for example, be extracted using information associated with a first set of determined driver gaze directions, and a second feature can be extracted using information associated with a second set of determined driver gaze directions. Moreover, in certain implementations the referenced features can be extracted using information associated with the first set of determined driver gaze directions and/or the second set of determined driver gaze directions.

The system is also configured to recognize the driver, and use stored/previously extracted features of the driver's eye(s) to calculate the driver gaze, and extract additional features of the driver's eye(s) while determining the relevant selected set of driver gaze (as described above) according to the gaze-direction (e.g., using the saved features of the driver's eye(s) from previous calibrations). In another example, the system can tag the certainty of the features extracted from the driver's eye(s) (e.g., a degree of certainty), and change, update, etc. the saved/stored features of the driver's eye(s) with a new set of features of the driver's eye(s), e.g., if the new set is tagged as being associated with higher certainty (e.g. a higher probability of accuracy).

By way of further illustration, the system can be configured to determine or decide when the driver is looking ahead, e.g., in a scenario in which vehicle 120 is moving at high speed (for example, faster than a speed of 50 mph or 65 mph). In another example, the system determines/decides when the driver is looking ahead in a scenario in which the vehicle is traveling on a highway, the vehicle is moving straight for a certain amount of time (T seconds), etc. The system can use data received from the camera looking forward to select the relevant gaze-direction set and filter out samples of gaze-direction that reflect a lower probability that the driver is looking ahead. For example, samples of gaze-direction can be selected as long as at that moment the other cars on the highway are determined to be moving in their lanes, and no car changed its lane (it can be appreciated that under such circumstances the user/driver is likely to be looking straight ahead).

In another implementation, the system uses data associated with the driver and/or vehicle (e.g., vehicle speed, sounds such as those from other vehicles on the road, and/or the driver behavior) to determine when a user/driver is likely looking ahead/forward. For example, a gaze-direction can be selected in response to a determination that the car is at least moving in a certain speed, no vehicles on the road changed their lane, and/or the driver hasn't picked up/looked at his phone. In another example, the system utilizes a combination of data associated with the direction of the car, the location of the car, the speed of the car and/or user behavior, to determine when a user/driver is likely looking ahead/forward, e.g., in a manner described herein.

Moreover, in certain implementations the system can further use data that reflects the location of where the driver is sitting. Such data can be received, for example, from the car, and can reflect the physical location at which the driver sitting, e.g., within the car. Such data can originate from sensors such as pressure sensors located within the driver seat, e.g., to determine the location of the driver and/or the driver's head.

It should be understood that, in various implementations, the described system can be configured to perform the described analysis of the data in real-time, offline and/or in 'the cloud' (e.g., on a remote device or machine).

Further aspects and implementations of the present disclosure relate reacting to changes in user attention using communication with a camera's image signal processor (ISP).

The presently disclosed subject matter may further comprise, responsive to a selection of a graphical element, receiving from the external device or website data relating to a graphical element identified in an image and presenting the received data to a user. The communication with the external device or website may be over a communication network.

Figure 5A:
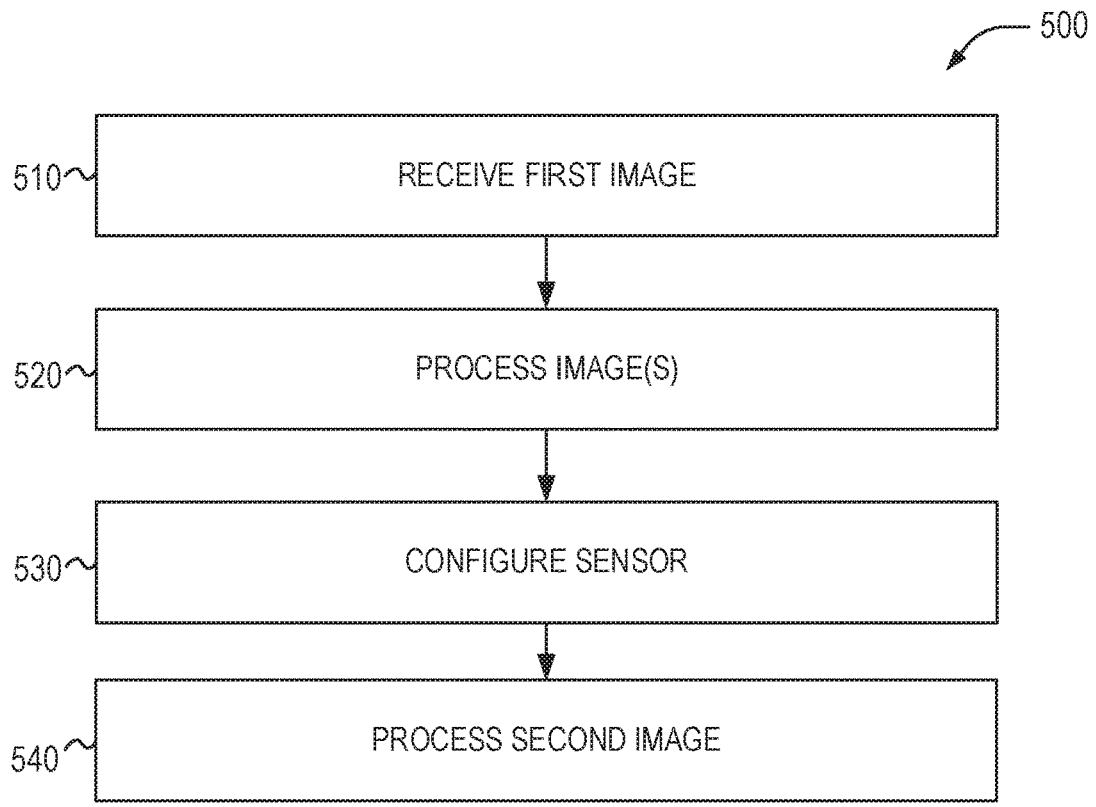
FIG. 5A is a flow chart illustrating a method, in accordance with an example embodiment.

FIG. 5A is a flow chart illustrating a method 500, according to an example embodiment, for reacting to changes in user attention using communication with a camera's ISP. Such methods are performed by processing logic that may comprise hardware (circuitry, dedicated logic, etc.), software (such as is run on a computer system or a dedicated machine), or a combination of both. In certain implementations, such methods can be performed by one or more devices, processor(s), machines, etc., including but not limited to those described and/or referenced herein. It should be understood that, in certain implementations, various operations, steps, etc., of methods/processes described and/or referenced herein may be performed by one or more of the processors/processing devices, sensors, and/or displays described and/or referenced herein, while in other embodiments some operations/steps may be performed other processing device(s), sensor(s), etc. Additionally, in certain implementations one or more operations/steps of the methods/processes described herein may be performed using a distributed computing system including multiple processors, and another processor in a networked device such as a mobile phone performing another step/operation. Furthermore, in some embodiments one or more steps of the described methods/processes may be performed using a cloud computing system.

It should also be noted that while the system described herein is illustrated with respect to reacting to changes in user attention using communication with a camera's ISP, the described system can also be implemented in any number of additional or alternative settings or contexts and towards any number of additional objectives.

In one example implementation, at operation 510 a first image captured by the image sensor is received. At operation 520, the first image is processed, e.g., to determine that the eye gaze of one or more eyes of a user is directed towards a road. At operation 530, based on a determination that the eye gaze of the user is directed towards the road, the image sensor is configured to transmit, to the at least one processor, a portion of a second image that corresponds to the eyes of the user. At operation 540, the portion of the second image that corresponds to the eyes of the user is processed.

Figure 5B:
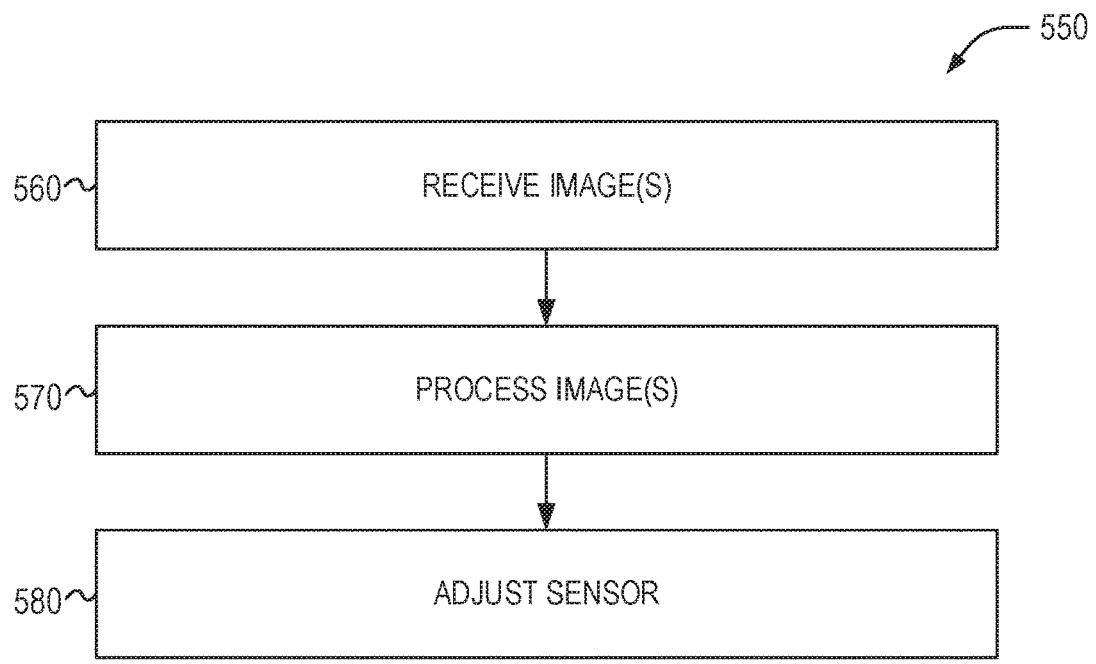
FIG. 5B is a flow chart illustrating a method, in accordance with an example embodiment.

FIG. 5B is a flow chart illustrating another method 550, according to an example embodiment. At operation 560, an image is received. At operation 570, the image is processed, e.g., to determine an eye gaze of one or more eyes of a user. In certain implementations, this can include determining an angle of the eye gaze of the user and/or determining that the user maintains the eye gaze for a defined period of time. At operation 580, based on the determination of the eye gaze of the user, one or more image processing parameters associated with the image sensor are adjusted. In certain implementations, this can include adjusting one or more image processing parameters with respect to coordinates within the image that correspond to the eyes of the user.

The described system includes systems and methods for capturing images, video, etc., such as of a human user. Such images, video, etc., can be processed to detect/determine the attention that the user is directing towards a particular item, task, etc. In certain implementations, upon determining that that a user is (or is not) directing his/her attention to a particular item, task, etc., various aspects, parameters, settings, etc., associated with the capture of the referenced images, video, etc., can be changed, adjusted, modified, etc. For example, based on various determination(s) (e.g., that a user is or is not directing their attention to the road ahead), power consumption, video transfer bandwidth (e.g., from the camera/image sensor to a processor) can be reduced, while maintaining a high image capture frame rate (e.g., 60 fps or 120 fps). Accordingly, also described herein are systems and methods for analyzing/processing image(s) to determine whether a driver is maintaining his/her eye gaze/focus on the road ahead (e.g., while driving), and cutting the power consumption/bandwidth of the images from the camera to the processor (and/or adjusting other parameters associated with the capture/processing of such images) while keeping the frame rate associated with the image(s) captured of the user at a high rate.

In certain implementations, the described systems and methods can be configured to analyze/process image(s) to determine whether a user is maintaining his/her eye gaze/focus on the road ahead (e.g., while driving). Upon determining that the driver is maintaining his/her eye gaze/focus (e.g., towards a road), an image sensor can be configured to transmit (e.g., to a processor) only a portion of subsequently captured image(s), e.g., the portion of such image(s) that correspond to the position of the eyes of the user. The reference portion of the captured image(s) (corresponding to the eyes of the user) can then be processed (e.g., to determine that the user is maintaining his/her gaze towards the road ahead). In doing so, the power consumption can be reduced by transmitting and processing only a subset of the captured images (i.e., the portion that corresponds to the eyes of the user), while keeping the frame rate associated with the image(s) captured of the user at a high rate and/or in high resolution.

In certain implementations, the described system can be configured to capture images, videos, etc. of the face, eyes, etc., of a user, and to process such images in order to track the gaze of the user, and to adjust the referenced settings, parameters, etc. (e.g., cutting/reducing power consumption, video transfer bandwidth from the camera to the processor, etc.) based on one or more determinations computed with respect to the gaze of the user. As noted above, the 'gaze of a user,' 'eye gaze,' etc., as described and/or referenced herein, can refer to the manner in which the eyes of a human user maintain their position/focus, e.g., over a period of time. For example, the 'eye gaze' of a user can refer to the direction towards which the eyes of such a user are directed or focused e.g., for an ongoing period of time. Additionally, in certain implementations the gaze of the user can be determined to be directed towards a particular item, object, task, etc. (e.g., directed towards the road ahead while driving) based on a determination that the eyes of the user are directed towards a particular angle/direction, which is associated with "looking on the road" and proper attention to driving or in relation to surrounding elements in the images/video, e.g., the inside car, and/or in other images/video). It should be understood that 'looking towards the road ahead' as referenced here can refer to a driver of a vehicle who directs/maintains the gaze/focus of his/her eyes towards the road that is visible through the front windshield of the car being driven (when driving in a forward direction). It can be appreciated that, for safety reasons, it is preferable (if not obligatory) that a driver maintain his/her eye gaze towards the road ahead during most (if not all) of the duration during which the user is driving the car.

For example, in certain implementations, upon determining that a user gaze is directed toward the road (e.g., the gaze of the user is within boundary of angle that that is defined as looking on the road) the described system can further process/analyze a portion of the captured image(s), video(s), etc. (for example the area that contains the user eyes) in order to further determine that the user is still looking on the road. Upon determining/recognizing that the user gaze is not directed towards the road ahead (or level of confidence of making such a determination is below a defined threshold, or the described system cannot identify/recognize user's eyes, etc.), the described systems and methods can be further configured to process/analyze a larger portion of the image/video (e.g., a portion determined to include the user's entire face) and/or to analyze even the entire image.

In certain implementations, the described system can receive images, videos, and/or other inputs from one or more sensors, e.g., an image sensor (e.g., a camera). Such image(s), video, etc. can be processed (e.g., using face detection techniques) to detect the presence of the eyes of the user. Upon detecting the eyes of the user, the gaze of the user can be determined. In certain implementations, the gaze of the user can be determined based on information such as the position of the camera in the car, the location of the user's face within the car (which may vary based on the height of the user), user age, gender, face structure, inputs from other sensors including camera that are positioned in different places in the car, sensors that provide 3D information of the user face (such as TOF sensors) or including IR camera, from external system etc.

Upon detecting/determining the gaze of the user, a region (e.g., of the image(s)) that contains the user's eyes can be defined. The coordinates (e.g., X, Y coordinates within the image) can then be transmitted, e.g., to an ISP (image signal processor) of the camera.

In one example, the detection of the user gaze or the user's eyes in the image is performed by a processor which is external to the camera, in another example the detection of the user gaze or the user's eyes in the image is performed by a processor which is integrated in the camera module, or in the ISP or performed by the ISP.

In another implementation, a detection is performed by the ISP or by a processor integrated in the camera module, and transmits to external processor a portion of the image including the user face, for further processing and analysis of user gaze detection.

Based on the received coordinates, the ISP can be configured to transmit a subset of the coming captured image to the processor for analysis, e.g., only the pixels within the coordinates that define the referenced region will be transmitted to the processor In doing so, the total power consumption of the system can be reduced, due to the reduced amount of data that is transmitted over the bus to the processor, and due to analysis by the processor on only a subset of the image and not all the image.

The described system can then process/analyze the referenced subset of the image. In doing so, it can be determined/verified whether the user gaze continues to be maintained within a range of defined direction, e.g., whether the user continues to be looking towards the road ahead. It should be understood that, in certain implementations, the position of the user's head, eyes, etc., may change (e.g., if they move their head). In such a scenario, such a change can be detected/determined, and corrected/updated coordinates can be provided to the ISP, if needed (for example, in a case that the user moved his head a bit but is still looking on the road).

Upon detecting, determining, recognizing, etc. that the user is not looking on the road (e.g., is not maintaining their gaze toward the road ahead) (or the described system determines that there is a suspicion that the user is not looking at the road, or the level of confidence of recognizing the gaze of the user is below a defined threshold, or the eyes of the user cannot be identified in the image, etc.), the described system can be configured to process, analyze, etc., a larger portion (or portions) of the image or to analyze the entire image, e.g., by transmitting new coordinates to the ISP which correspond to a larger portion of the image (or the entire image).

In one example, the described system can be configured to detect and/or disregard blinking events (e.g. when user blinks, the "gaze" of the user is momentarily not directed towards the road). The detection and/or disregard of the blinking event can be performed by a processor which is external to the camera. In another example the detection of the user gaze or the user's eyes in the image is performed by a processor which is integrated in the camera module, or in the ISP or performed by the ISP.

In order to detect the gaze of users who wear glasses, sun glasses, etc., the described system can utilize/apply face recognition techniques that detect faces with glasses (for example, using classifiers that were trained on users with glasses, and sun glasses).

In case the user is wearing sunglasses, the detection of the gaze may account for/be computed (at least in part) based on the direction towards which the user's face is facing, using information such as the location of the camera in the car, the position user face of the user face in relation, etc.

It should be understood that, with respect to determining/detecting user gaze, the quality of the image in total may be of less importance, while it may be more important to have as much visual information related to the user's face. Accordingly, the described system may be configured to provide coordinates to the ISP with which to compute the image parameters such as exposure, coordination of the user face. In such manner, the described system can verify that those significant aspects of the image are in its best visual quality, and areas around the user, including information from parts of the image such as the car windows, can be deemphasized or neglected (with respect to the visual quality of image in these areas, for example, they may be completely dark, or completely 'burned,' etc.).

In certain implementations, the described technologies can further include a system and/or a method for recognizing user gaze. Such a system can include an image sensor, at least one image of a viewing space of an image sensor. The at least one image can be processed by at least one processor, and data indicative of a location of a face or eyes of a user (or driver) within the image can be obtained. A subset of the image can be determined in relation to the detected user face/eyes (e.g., subset of the image can contain the detected user's face/eyes). In certain implementations, the system can be configured to alter the image sensor or ISP parameters according to the visual data associated with the image information within the determined subset of the image and detect the user gaze in images following altering the ISP parameters. In another example, the system can iteratively alter the image sensor(s) or ISP parameters according to parameters associated with the level of detection of the user gaze. In certain implementations, the image sensor or ISP can iteratively alter parameters until reaching optimum parameter(s) for user gaze detection.

Further aspects of the described system are depicted in various figures. For example, FIG. 1 depicts aspects of extracting, determining, etc. the eye gaze of a user (e.g., a driver of a car), e.g., using information that may include the position of the camera in the car, the location of the user face in the car (which can vary widely according the user height), user age, gender, face structure, etc., as described herein. As shown in FIG. 1, driver 110 can be seated in car 120 (it should be understood that the described system can be similarly employed with respect to practically any vehicle, e.g., bus, etc.), and the gaze/position of the eyes of the user position can be determined based on images captured by camera 130 as positioned within the car. It should also be noted that 'car' as used herein can refer to practically any motor vehicle used for transportation, such as a wheeled, self-powered motor vehicle, flying vehicle, etc.

Figure 6:
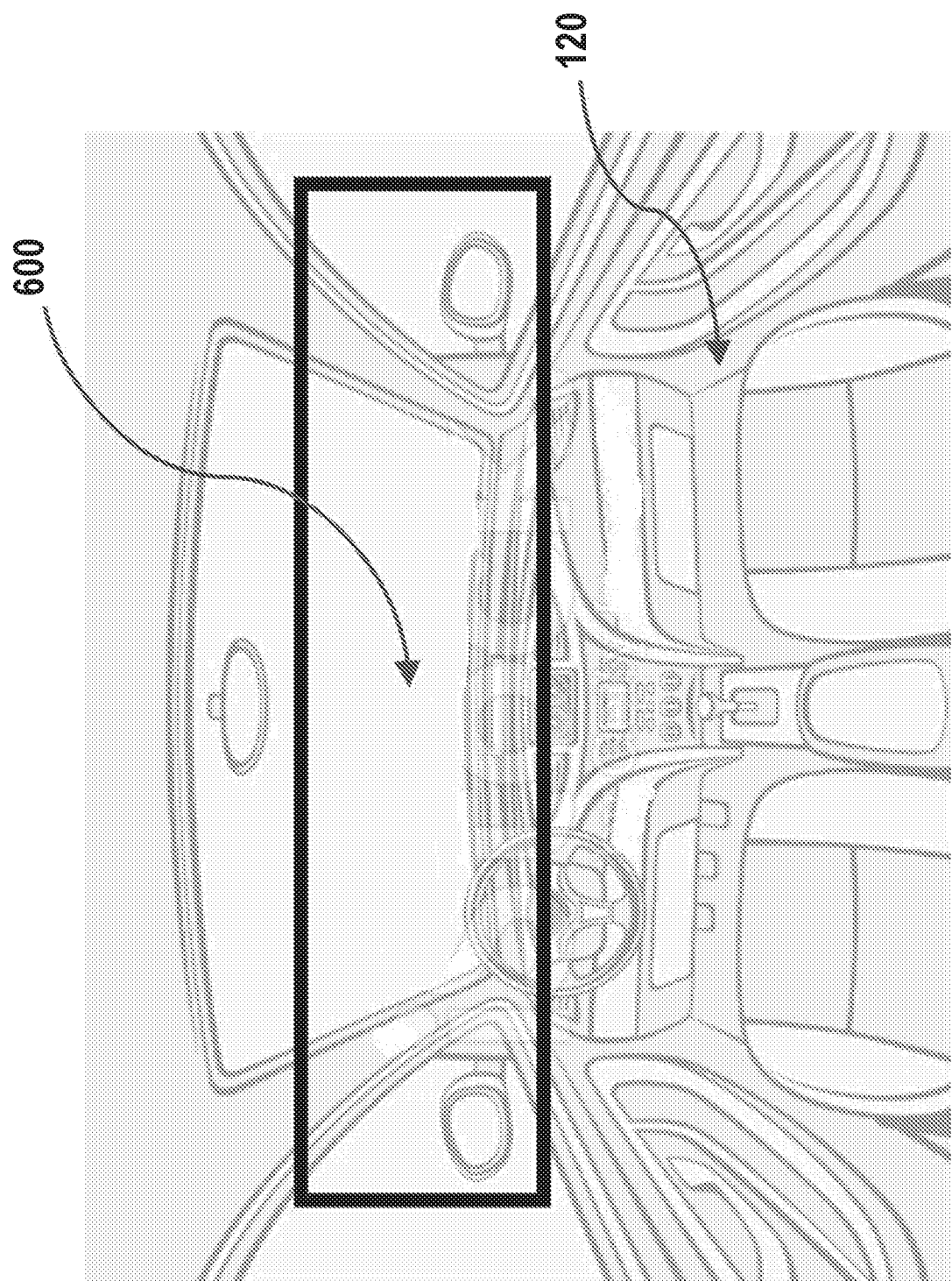
FIG. 6 illustrates an example scenario described herein, according to an example embodiment.

FIG. 6 depicts an example region 600 within car 120 which reflects the angle of the driver gaze that may be considered as looking towards the road ahead. If a user gaze is determined to be outside the angle of region 600 it can be determined that the driver is not looking on the road.

Figure 7A:
FIG. 7A illustrates an example scenario described herein, according to an example embodiment.
Figure 7B:
FIG. 7B illustrates an example scenario described herein, according to an example embodiment.

FIGS. 7A and 7B depict examples of a user gaze where user is not looking towards the road ahead. In such circumstances, the described system can be configured to analyze a greater subset of the image or even the full image.

Also described herein are systems, methods, and related technologies for detecting driver body posture. The described systems and methods can be directed to capturing images, video, etc., of the interior of a car. In certain implementations, such images can be processed to detect the presence of a human user within the car (e.g., the driver of the car). More specifically, the image(s) of the interior of the car can be processed/analyzed to identify/detect various parts of the body of the driver in order to determine the body posture of the driver (e.g., while driving) in high fidelity. The detection of the body posture can then be accounted with respect to providing various instructions/initiating various actions/commands. For example, a determination or detection of the body posture of a driver can be used to determine which airbag within a vehicle to inflate in the event of an accident.

Figure 8:
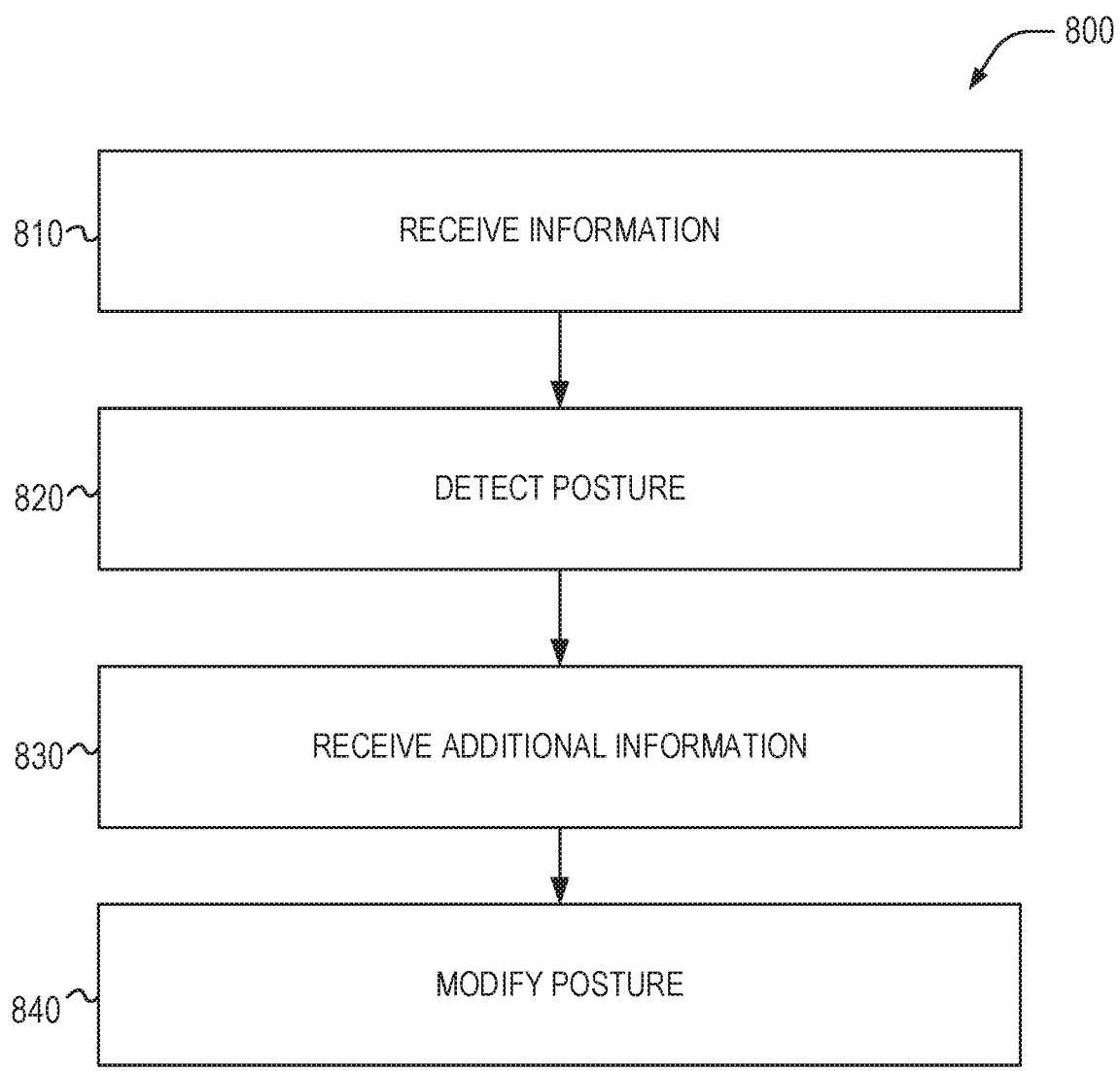
FIG. 8 is a flow chart illustrating a method, in accordance with an example embodiment.

FIG. 8 is a flow chart illustrating a method 800, according to an example embodiment. At operation 810, image information associated with space within the car is received, e.g., from an image sensor. At operation 820, the driver body posture is detected, e.g., in the image information. At operation 830, additional information is received, e.g., information other than the information from the image sensor. Such additional information can be, for example, may be the location in space of the driver in the car (e.g., the distance of the driver's seat from the steering wheel, the location of the driver body parts as extracted from another sensor rather than the image sensor, etc.). In certain implementations, such additional information may be associated with information of the driver body posture in similar detected body posture in the past where the conditions of detection where optimal. In certain implementations, the additional information may be in part related to locations and relation between body joints in predefined body posture. In certain implementations, the driver body posture may be detected at least in part based on detecting location of driver body joints. In certain implementations, the additional information may be information extracted from a database representing the joint location and other driver body parts in a body posture that is aligned with the detected body posture. In certain implementations, the additional information may be the driver body dimensions. In certain implementations, the driver body dimensions includes the driver height. At operation 840, the additional information is used to modify or validate the detected driver body posture.

In order to detect the body posture of the driver with a high degree of robustness (e.g., accuracy), the described system can further use/account for additional information, together with the data/inputs received from the image sensor, in order to detect the driver's body posture. Such 'additional information' may originate from various sources, and may be used to validate and/or modify the determination of the body posture of the user (e.g., as previously detected/ determined based on the captured image).

In certain implementations, the body posture of the driver can be detected based at least in part on the recognition of the body joints of the driver, and/or the location of pre-defined body parts (such as head, neck, arms etc.).

The referenced additional information (which, as noted, can also be accounted for in determining/detecting the body posture of the driver) can be, for example, a detection of a predefined body posture of the driver in previous frame(s)/ images (e.g. detection of the driver placing his two hands on the steering wheel of the vehicle) and using information associated with such predefined body posture (for example, information regarding the location in space of the driver's body parts and joints in such a predefined body posture), to validate and/or correct (if needed) the detected body posture of the driver as extracted/determined from information extracted from the image sensor.

For example, upon detecting that the driver is placing two hands on the steering wheel, in certain location on the wheel, additional information to enhance, correct and/or validate the detection of the body posture of the driver (e.g., as determined from information extracted from the image sensor) can be utilized, such as information extracted from a database representing the location of joint(s) and other body parts of the driver while the driver's body posture reflects that he/she is placing their hands on the steering wheel.

Other additional information (which, as noted, can also be accounted for in determining/detecting the body posture of the driver) can be associated with body dimension(s) of the driver (e.g., the driver's height, which is information that can be extracted from a database, for example), the location in space of the driver within the car (e.g., the distance between the driver's seat and the steering wheel, or the location of body part(s) of the driver as extracted from another sensor such as TOF sensor, pressure sensors located in the driver's seat, and/or any other sensor that can provide such information), information of the body posture of the driver in a similar detected body posture in the past (e.g., where the conditions of detection where optimal), etc.

The referenced additional information (which, as noted, can also be accounted for in determining/detecting the body posture of the driver) can also be associated with a user behavior (yawning, for example) and various gesture(s) associated with it (such as the user may reach their hand towards their mouth, for example).

The described system may utilize a subset or all of the additional information to assist/enhance the detection of the body posture of the driver, validate and/or correct the detection of the driver body joints or other body parts.

Furthermore, making such detections with high fidelity (e.g. detection when there is a priori knowledge/information of the driver posture such as when driver places his two hands on the steering wheel, knowledge/information of what are the locations and the relation in distance of the joints and body in such a posture) may be accounted for/used to assist in detection of the body posture of the driver in other detected postures (e.g. when the detected posture is not aligned with predefined posture in the database), as the changing between one posture to another is a linear movement (no matter how fast the movement is), and information of high fidelity of body posture detection at a first moment in time ('T1') can assist in detection of body posture at a second moment in time ('T2').

The system may relate to the referenced moments of high fidelity as "docking points" within the process of continuous detection of the body posture of the driver. An example docking point can be moment(s) in time where the detection of the body posture of the driver is made with high fidelity, or the referenced additional information associated with the detected predefined driver body posture is utilized.

In one example, the system tags some or each of the body posture of the detected user (driver) with a value that reflects the level of fidelity (accuracy) in recognizing the user body posture. The system may use the tagging to classified "docking points".

In one example, the system uses information that reflects the probability that a user (a driver) is to move from a first body posture to a second body posture.

Also described herein are an automotive system and method to detect/determine the attention of a driver. In certain implementations, such an automotive system can be configured to overcome a quick change of light, e.g., shining on the face of the driver, and to set the camera with the correct exposure level (e.g., an exposure level that enables stable quality of visual information to be detected with respect to the user's face).

Such a quick change of light over the driver's face can occur at night, for example, when the car travels past a street light, or when a car traveling on the other side of the road is approaching. The change in the amount of light over the face of the driver may be very significant and such a change may take place very quickly.

It can be appreciated that it may possible to overcome such a quick change by increasing the FPS (frames per second) of the image sensor, however doing so is likely to also increase power consumption.

The system can be configured to predict the change of light on the face of the driver, using information from external sensors (e.g., sensors that scan/look outside of the car and can, for example, recognize light from a car approaching from the other side, or street lights, or getting in/out of a channels, etc.), or extracted from previous images, as detecting a repeated sequence of increase of light (for example created by street lights), or from other sources of information including but not limited to maps, or data related to the roads, or data from other cars.

Following the referenced prediction, the system can transmit the information to the image sensor (e.g., the image signal processor (ISP)), to be used in its calculation of exposure.

In another example, the system may be or include an ISP that computes exposure based on information extracted from the image sensor and information received from other sources, such as information from external sensors (sensors that scan/look outside of the car and can, for example, recognize light from a car approaching from the other side, or street lights, or getting in/out of a channel, etc.), or extracted from previous images, as detecting a repeated sequence of increase of light (for example created by street lights), or from other sources of information including maps, or data related to the roads, or data from other cars, or a system running on CPU analyzing the image captured by image sensor to which the ISP is related, a system that extract information related to the user, including the detecting his face or direction of gaze.

In one example, a system and method is provided for driver monitoring and/or detection of driver gaze, e.g., by altering the image sensor or ISP parameters; using information in addition to the information extracted from the image sensor facing toward the driver to predict and set the parameters of the image sensor facing toward the driver to achieve optimal information for detection of driver related features (such as driver gaze, driver emotional respond, driver alertness etc.).

In one example, the system and method combines information from different sources; for example a sensor facing outside and may provide information pertaining to a reflection of a light from a car approaching from the other side, or street lights, or getting in/out of a channel, etc., calculate and combines it with the speed of the car to predict when it will be required to alter the image sensor (ISP) parameters to prevent the face of the driver to be "burned" by the light from the external source (car, street light etc.).

In another example, the system and method uses the additional information associated with a sudden change of light over the driver face and eyes when analyzing the features of the driver eyes (such as the size of the pupil) to detect the driver gaze.

In another example, the system and method can predict if the driver will be blinded (in which during the "blinding period" the driver's ability to respond to events taking place on the road can be reduced) and control parameters of the car (e.g. speed, direction of the car) in a different manner compare to the state in which the driver is not blinded.

Also described herein are systems and methods for predicting the body posture of a driver using information from at least one accelerator. In certain implementations, such a system can recognize/determine the body posture of a driver using information associated with data extracted from at least one accelerators located in the car.

Additionally, in certain implementations, in the event of an impact in the car where the change of the driver posture is high (and the image might be blurred), the system can utilize information extracted from image sensor prior to the impact (e.g., at T milliseconds before the impact) and information from the accelerator as leading information within the moment of impact.

Also described herein are systems and methods for extracting/identifying hand joints using deep learning and/or machine learning. In certain implementations, 2D and 3D images of the same hand can be used to train a deep learning machine. In doing so, the hand joints can be identified/extracted from an input of 2D images only.

Also described herein are systems and methods for tracking a driver within a car.

It can be appreciated that one of the best places within the car to locate/orient a camera in order to detect the driver's attention, body posture and other driver behavior, is the location of the windshield. However, positioning a camera on the windshield can disturb the field of view of the camera, e.g., while taking it down or when it is in between positions.

Accordingly, the described system can overcome this challenge/shortcoming by detecting when the windshield is in a position that interferes with the camera's field of view, and signaling to the driver (e.g., to pull it down fully or place if back).

Other options include adding in the windshield design a module that doesn't enable the windshield to be in a position of interfering to the camera. For example, a string can be employed that, when the windshield is within a certain angle (which is also the angle that interferes with the camera), the windshield is automatically moved (by the string) into an opened or closed position.

Another option can be to design the windshield in a manner that it will not interface with the camera field of view, and/or make it from a material that is transparent to IR.

Another option can be that the windshield can be controlled by an electric engine that swings it from one position to the other, and such an engine can be configured to not enable the windshield to be oriented/positioned at angles that interfere with the camera.

Figure 9:
FIG. 9 illustrates an example scenario described herein, according to an example embodiment.

Further aspects of the described system are described herein in relation to various Figures. FIG. 9 depicts an example scenario of a driver seated in a predefined posture, such as two hands on the steering wheel. As described herein, such posture can be defined/determined based on user joints 900 and other body parts.

Figure 10:
FIG. 10 illustrates an example scenario described herein, according to an example embodiment.

FIG. 10 depicts an example scenario of another driver seated in a predefined posture (two hands on the steering wheel). As described herein, such posture can be defined/determined based on user joints and other body parts. As shown in FIG. 10, the referenced additional information (based upon which the driver's posture can be verified) can be related specifically to the driver who is currently driving the car now.

Figure 11:
FIG. 11 illustrates an example scenario described herein, according to an example embodiment.

FIG. 11 depicts example(s) 1100 of the referenced additional information which can be used to verify/modify various determinations (e.g., the posture of the driver), such as information relating to the driver space (e.g., location of the driver's seat, the distance between the seat and the steering wheel, the height of the seat, etc.). It can be appreciated that different drivers and different cars may reflect different driver spaces, yet for a particular car and driver, such the space is very much constant.

FIGS. 7A and 7B depict examples of learning the body posture of the driver while being in the car, e.g., while the car is stopped (e.g., when at a traffic light) and during driving.

It should also be noted that while the technologies described herein are illustrated primarily with respect to driver monitoring, the described technologies can also be implemented in any number of additional or alternative settings or contexts and towards any number of additional objectives. It should be understood that further technical advantages, solutions, and/or improvements (beyond those described and/or referenced herein) can be enabled as a result of such implementations.

For example, in certain implementations the described system can be applied in a scenario (that may not involve a vehicle) in which there is a predefined location at which the user looks at. In such a scenario, the described technologies can recognize the user gaze-direction and correlate the detected user gaze-direction with the predefined location(s) the user may be/is likely to be looking at. A set of gaze-directions can be selected from the total detected gaze-directions for each predefined location. A set of samples within the determined set can (optionally) be selected. Features of the user's eye(s) can be extracted using the data associated with the selected set of user gaze-direction, the location of the user (including the location and orientation of the user's head), and the locations of the objects (which can also be digital visual objects) associated with each set.

It should be noted that the described technologies may be implemented within and/or in conjunction with various devices or components such as any digital device, including but not limited to: a personal computer (PC), an entertainment device, set top box, television (TV), a mobile game machine, a mobile phone or tablet, e-reader, smart watch, digital wrist armlet, game console, portable game console, a portable computer such as laptop or ultrabook, all-in-one, TV, connected TV, display device, a home appliance, communication device, air-condition, a docking station, a game machine, a digital camera, a watch, interactive surface, 3D display, an entertainment device, speakers, a smart home device, IoT device, IoT module, smart window, smart glass, smart light bulb, a kitchen appliance, a media player or media system, a location based device; and a mobile game machine, a pico projector or an embedded projector, a medical device, a medical display device, a vehicle, an in-car/in-air Infotainment system, drone, autonomous car, self-driving car, flying vehicle, navigation system, a wearable device, an augment reality enabled device, a wearable goggles, a virtual reality device, a location based device, a robot, social robot, android, interactive digital signage, digital kiosk, vending machine, an automated teller machine (ATM), and/or any other such device that can receive, output and/or process data.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "receiving," "processing," "providing," "identifying," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Aspects and implementations of the disclosure also relate to an apparatus for performing the operations herein. A computer program to activate or configure a computing device accordingly may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The present disclosure is not described with reference to any particular programming language. It will be appreciated that a variety of programming languages may be used to implement the teachings of the disclosure as described herein.

As used herein, the phrase "for example," "such as," "for instance," and variants thereof describe non-limiting embodiments of the presently disclosed subject matter. Reference in the specification to "one case," "some cases,"

"other cases," or variants thereof means that a particular feature, structure or characteristic described in connection with the embodiment(s) is included in at least one embodiment of the presently disclosed subject matter. Thus the appearance of the phrase "one case," "some cases," "other cases," or variants thereof does not necessarily refer to the same embodiment(s).

Certain features which, for clarity, are described in this specification in the context of separate embodiments, may also be provided in combination in a single embodiment. Conversely, various features which are described in the context of a single embodiment, may also be provided in multiple embodiments separately or in any suitable sub combination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments have been described. Other embodiments are within the scope of the following claims.

Certain implementations are described herein as including logic or a number of components, modules, or mechanisms. Modules can constitute either software modules (e.g., code embodied on a machine-readable medium) or hardware modules. A "hardware module" is a tangible unit capable of performing certain operations and can be configured or arranged in a certain physical manner. In various example implementations, one or more computer systems (e.g., a standalone computer system, a client computer system, or a server computer system) or one or more hardware modules of a computer system (e.g., a processor or a group of processors) can be configured by software (e.g., an application or application portion) as a hardware module that operates to perform certain operations as described herein.

In some implementations, a hardware module can be implemented mechanically, electronically, or any suitable combination thereof. For example, a hardware module can include dedicated circuitry or logic that is permanently configured to perform certain operations. For example, a hardware module can be a special-purpose processor, such as a Field-Programmable Gate Array (FPGA) or an Application Specific Integrated Circuit (ASIC). A hardware module can also include programmable logic or circuitry that is temporarily configured by software to perform certain operations. For example, a hardware module can include software executed by a general-purpose processor or other programmable processor. Once configured by such software, hardware modules become specific machines (or specific components of a machine) uniquely tailored to perform the configured functions and are no longer general-purpose processors. It will be appreciated that the decision to implement a hardware module mechanically, in dedicated and permanently configured circuitry, or in temporarily configured circuitry (e.g., configured by software) can be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering implementations in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor can be configured as respectively different special-purpose processors (e.g., comprising different hardware modules) at different times. Software accordingly configures a particular processor or processors, for example, to constitute a particular hardware module at one instance of time and to constitute a different hardware module at a different instance of time.

Hardware modules can provide information to, and receive information from, other hardware modules. Accordingly, the described hardware modules can be regarded as being communicatively coupled. Where multiple hardware modules exist contemporaneously, communications can be achieved through signal transmission (e.g., over appropriate circuits and buses) between or among two or more of the hardware modules. In implementations in which multiple hardware modules are configured or instantiated at different times, communications between such hardware modules can be achieved, for example, through the storage and retrieval of information in memory structures to which the multiple hardware modules have access. For example, one hardware module can perform an operation and store the output of that operation in a memory device to which it is communicatively coupled. A further hardware module can then, at a later time, access the memory device to retrieve and process the stored output. Hardware modules can also initiate communications with input or output devices, and can operate on a resource (e.g., a collection of information).

The various operations of example methods described herein can be performed, at least partially, by one or more processors that are temporarily configured (e.g., by software) or permanently configured to perform the relevant operations. Whether temporarily or permanently configured, such processors can constitute processor-implemented modules that operate to perform one or more operations or functions described herein. As used herein, "processor-implemented module" refers to a hardware module implemented using one or more processors.

Similarly, the methods described herein can be at least partially processor-implemented, with a particular processor or processors being an example of hardware. For example, at least some of the operations of a method can be performed by one or more processors or processor-implemented modules. Moreover, the one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., an API).

The performance of certain of the operations can be distributed among the processors, not only residing within a single machine, but deployed across a number of machines. In some example implementations, the processors or processor-implemented modules can be located in a single geographic location (e.g., within a home environment, an office environment, or a server farm). In other example implementations, the processors or processor-implemented modules can be distributed across a number of geographic locations.

The modules, methods, applications, and so forth described in conjunction with FIGS. 1-11 are implemented in some implementations in the context of a machine and an associated software architecture.

The sections below describe representative software architecture(s) and machine (e.g., hardware) architecture(s) that are suitable for use with the disclosed implementations.

Software architectures are used in conjunction with hardware architectures to create devices and machines tailored to particular purposes. For example, a particular hardware architecture coupled with a particular software architecture will create a mobile device, such as a mobile phone, tablet device, or so forth. A slightly different hardware and software architecture can yield a smart device for use in the "internet of things," while yet another combination produces a server computer for use within a cloud computing architecture. Not all combinations of such software and hardware architectures are presented here, as those of skill in the art can readily understand how to implement the inventive subject matter in different contexts from the disclosure contained herein.

FIG. 12 is a block diagram illustrating components of a machine 1200, according to some example implementations, able to read instructions from a machine-readable medium (e.g., a machine-readable storage medium) and perform any one or more of the methodologies discussed herein. Specifically, FIG. 12 shows a diagrammatic representation of the machine 1200 in the example form of a computer system, within which instructions 1216 (e.g., software, a program, an application, an applet, an app, or other executable code) for causing the machine 1200 to perform any one or more of the methodologies discussed herein can be executed. The instructions 1216 transform the general, non-programmed machine into a particular machine programmed to carry out the described and illustrated functions in the manner described. In alternative implementations, the machine 1200 operates as a standalone device or can be coupled (e.g., networked) to other machines. In a networked deployment, the machine 1200 can operate in the capacity of a server machine or a client machine in a server-client network environment, or as a peer machine in a peer-to-peer (or distributed) network environment. The machine 1200 can comprise, but not be limited to, a server computer, a client computer, PC, a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1216, sequentially or otherwise, that specify actions to be taken by the machine 1200. Further, while only a single machine 1200 is illustrated, the term "machine" shall also be taken to include a collection of machines 1200 that individually or jointly execute the instructions 1216 to perform any one or more of the methodologies discussed herein.

The machine 1200 can include processors 1210, memory/storage 1230, and I/O components 1250, which can be configured to communicate with each other such as via a bus 1202. In an example implementation, the processors 1210 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) can include, for example, a processor 1212 and a processor 1214 that can execute the instructions 1216. The term "processor" is intended to include multi-core processors that can comprise two or more independent processors (sometimes referred to as "cores") that can execute instructions contemporaneously. Although FIG. 12 shows multiple processors 1210, the machine 1200 can include a single processor with a single core, a single processor with multiple cores (e.g., a multi-core processor), multiple processors with a single core, multiple processors with multiples cores, or any combination thereof.

The memory/storage 1230 can include a memory 1232, such as a main memory, or other memory storage, and a storage unit 1236, both accessible to the processors 1210 such as via the bus 1202. The storage unit 1236 and memory 1232 store the instructions 1216 embodying any one or more of the methodologies or functions described herein. The instructions 1216 can also reside, completely or partially, within the memory 1232, within the storage unit 1236, within at least one of the processors 1210 (e.g., within the processor's cache memory), or any suitable combination thereof, during execution thereof by the machine 1200. Accordingly, the memory 1232, the storage unit 1236, and the memory of the processors 1210 are examples of machine-readable media.

As used herein, "machine-readable medium" means a device able to store instructions (e.g., instructions 1216) and data temporarily or permanently and can include, but is not limited to, random-access memory (RAM), read-only memory (ROM), buffer memory, flash memory, optical media, magnetic media, cache memory, other types of storage (e.g., Erasable Programmable Read-Only Memory (EEPROM)), and/or any suitable combination thereof. The term "machine-readable medium" should be taken to include a single medium or multiple media (e.g., a centralized or distributed database, or associated caches and servers) able to store the instructions 1216. The term "machine-readable medium" shall also be taken to include any medium, or combination of multiple media, that is capable of storing instructions (e.g., instructions 1216) for execution by a machine (e.g., machine 1200), such that the instructions, when executed by one or more processors of the machine (e.g., processors 1210), cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 1250 can include a wide variety of components to receive input, provide output, produce output, transmit information, exchange information, capture measurements, and so on. The specific I/O components 1250 that are included in a particular machine will depend on the type of machine. For example, portable machines such as mobile phones will likely include a touch input device or other such input mechanisms, while a headless server machine will likely not include such a touch input device. It will be appreciated that the I/O components 1250 can include many other components that are not shown in FIG. 12. The I/O components 1250 are grouped according to functionality merely for simplifying the following discussion and the grouping is in no way limiting. In various example implementations, the I/O components 1250 can include output components 1252 and input components 1254. The output components 1252 can include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1254 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example implementations, the I/O components 1250 can include biometric components 1256, motion components 1258, environmental components 1260, or position components 1262, among a wide array of other components. For example, the biometric components 1256 can include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1258 can include acceleration sensor components (e.g., accelerometer), gravitation sensor components, rotation sensor components (e.g., gyroscope), and so forth. The environmental components 1260 can include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that can provide indications, measurements, or signals corresponding to a surrounding physical environment. The position components 1262 can include location sensor components (e.g., a Global Position System (GPS) receiver component), altitude sensor components (e.g., altimeters or barometers that detect air pressure from which altitude can be derived), orientation sensor components (e.g., magnetometers), and the like.

Communication can be implemented using a wide variety of technologies. The I/O components 1250 can include communication components 1264 operable to couple the machine 1200 to a network 1280 or devices 1270 via a coupling 1282 and a coupling 1272, respectively. For example, the communication components 1264 can include a network interface component or other suitable device to interface with the network 1280. In further examples, the communication components 1264 can include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1270 can be another machine or any of a wide variety of peripheral devices (e.g., a peripheral device coupled via a USB).

Moreover, the communication components 1264 can detect identifiers or include components operable to detect identifiers. For example, the communication components 1264 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information can be derived via the communication components 1264, such as location via Internet Protocol (IP) geolocation, location via Wi-Fi® signal triangulation, location via detecting an NFC beacon signal that can indicate a particular location, and so forth.

In various example implementations, one or more portions of the network 1280 can be an ad hoc network, an intranet, an extranet, a virtual private network (VPN), a local area network (LAN), a wireless LAN (WLAN), a WAN, a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 1280 or a portion of the network 1280 can include a wireless or cellular network and the coupling 1282 can be a Code Division Multiple Access (CDMA) connection, a Global System for Mobile communications (GSM) connection, or another type of cellular or wireless coupling. In this example, the coupling 1282 can implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 1216 can be transmitted or received over the network 1280 using a transmission medium via a network interface device (e.g., a network interface component included in the communication components 1264) and utilizing any one of a number of well-known transfer protocols (e.g., HTTP).

Similarly, the instructions 1216 can be transmitted or received using a transmission medium via the coupling 1272 (e.g., a peer-to-peer coupling) to the devices 1270. The term "transmission medium" shall be taken to include any intangible medium that is capable of storing, encoding, or carrying the instructions 1216 for execution by the machine 1200, and includes digital or analog communications signals or other intangible media to facilitate communication of such software.

Throughout this specification, plural instances can implement components, operations, or structures described as a single instance. Although individual operations of one or more methods are illustrated and described as separate operations, one or more of the individual operations can be performed concurrently, and nothing requires that the operations be performed in the order illustrated. Structures and functionality presented as separate components in example configurations can be implemented as a combined structure or component. Similarly, structures and functionality presented as a single component can be implemented as separate components. These and other variations, modifications, additions, and improvements fall within the scope of the subject matter herein.

Although an overview of the inventive subject matter has been described with reference to specific example implementations, various modifications and changes can be made to these implementations without departing from the broader scope of implementations of the present disclosure. Such implementations of the inventive subject matter can be referred to herein, individually or collectively, by the term "invention" merely for convenience and without intending to voluntarily limit the scope of this application to any single disclosure or inventive concept if more than one is, in fact, disclosed.

The implementations illustrated herein are described in sufficient detail to enable those skilled in the art to practice the teachings disclosed. Other implementations can be used and derived therefrom, such that structural and logical substitutions and changes can be made without departing from the scope of this disclosure. The Detailed Description, therefore, is not to be taken in a limiting sense, and the scope of various implementations is defined only by the appended claims, along with the full range of equivalents to which such claims are entitled.

As used herein, the term "or" can be construed in either an inclusive or exclusive sense. Moreover, plural instances can be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and can fall within a scope of various implementations of the present disclosure. In general, structures and functionality presented as separate resources in the example configurations can be implemented as a combined structure or resource. Similarly, structures and functionality presented as a single resource can be implemented as separate resources. These and other variations, modifications, additions, and improvements fall within a scope of implementations of the present disclosure as represented by the appended claims. The specification and drawings are, accordingly, to be regarded in an illustrative rather than a restrictive sense.

What is claimed is:

1. A system comprising:
   at least one image sensor; and
   at least one processor, configured to:
      receive one or more images from the image sensor, the one or more images reflecting at least a portion of a face of a driver;
      determine, using the images, a direction of a gaze of the driver;
      identify a set of determined driver gaze directions comprising a first location at which the driver is looking at a first point in time and a second location at which the driver is looking at a second point in time;
      correlate the determined driver gaze directions with at least one predefined direction; and
      extract one or more features of one or more eyes of the driver using information associated with the identified set of determined driver gaze directions.

2. The system of claim 1, wherein the direction of the gaze of the driver reflects a location at which the driver is looking.

3. The system of claim 2, wherein the location reflects a location outside a vehicle within which the driver is present.

4. The system of claim 2, wherein the location further reflects a location inside a vehicle within which the driver is present.

5. The system of claim 1, wherein to identify the set of determined driver gaze directions, the at least one processor is further configured to correlate one or more of the determined driver gaze directions with the at least one predefined direction.

6. The system of claim 1, wherein the set of determined driver gaze directions is identified using information associated with a distribution of the driver gaze during driving.

7. The system of claim 6, wherein the set of determined driver gaze directions is identified using at least one of: information associated with a distribution of the driver gaze outside during driving; information associated with a distribution of the driver gaze inside a vehicle while driving; information associated with a distribution of the driver gaze based on driving behavior; information associated with a distribution of the driver gaze based on one or more actions of the driver occurring within a vehicle; information associated with a distribution of the driver gaze based on one or more actions of the driver occurring in relation to a component of a vehicle; or additional information associated with at least one of: a motion direction of a vehicle, a vehicle speed, or a geographic location of a vehicle.

8. The system of claim 1, wherein to extract the one or more features, the at least one processor is further configured to extract respective features from each of the determined driver gaze directions within the set.

9. The system of claim 1,
   wherein to identify a set of determined driver gaze directions the processor is further configured to identify at least a first set of driver gaze directions and a second set of driver gaze directions; and
   wherein to extract the one or more features, the at least one processor is further configured to extract at least a first feature using information associated with the first set of determined driver gaze directions and a second feature from the second set of determined driver gaze directions.

10. The system of claim 1,
    wherein to identify a set of determined driver gaze directions the processor is further configured to identify at least a first set of driver gaze directions and a second set of driver gaze directions; and
    wherein to extract the one or more features, the at least one processor is further configured to extract the one or more features using information associated with at least the first set of determined driver gaze directions and the second set of determined driver gaze directions.

11. The system of claim 1, wherein the at least one processor is further configured to determine a position of a head of the driver.

12. The system of claim 11, wherein to identify the set of determined driver gaze directions, the at least one processor is further configured to identify the set of determined driver gaze directions using at least one of: the position of the head of the driver or information associated with a position of the head of the driver.

13. The system of claim 1, further comprising a light emitting device.

14. The system of claim 13, wherein the light emitting device comprises an infrared (IR) light emitting device.

15. The system of claim 1, wherein to identify the set of determined driver gaze directions, the at least one processor is further configured to identify the set of determined driver gaze directions using a position of one or more objects inside a vehicle within which the driver is present.

16. The system of claim 15, wherein the one or more objects include one or more mirrors of the vehicle.

17. The system of claim 1, wherein the at least one predefined direction reflects a direction aligned with the direction of the motion of the vehicle within which the driver is present is traveling.

18. The system of claim 1, wherein the one or more features comprises at least one of: a kappa angle of the one or more eyes of the driver, a radius of curvature of a cornea of the driver, or a distance between (a) a pupil plane of the one or more eyes of the driver and (b) a center of curvature of a cornea of the driver.

19. A method comprising:
receiving one or more images from an image sensor, the one or more images reflecting a at least a portion of a face of a driver;
determining, using the images, a direction of a gaze of the driver;
identifying a set of determined driver gaze directions comprising a first location at which the driver is looking at a first point in time and a second location at which the driver is looking at a second point in time;
correlating the determined driver gaze directions with at least one predefined direction; and
extracting one or more features of one or more eyes of the driver using information associated with the identified set of determined driver gaze directions.

20. A non-transitory computer readable medium having instructions stored thereon that, when executed by a processing device, cause the processing device to perform operations comprising:
receiving one or more images from an image sensor, the one or more images reflecting a at least a portion of a face of a user;
determining, using the images, a direction of a gaze of the user;
identifying a set of determined user gaze directions comprising a first location at which the driver is looking at a first point in time and a second location at which the driver is looking at a second point in time;
correlating the determined driver gaze directions with at least one predefined direction; and
extracting one or more features of one or more eyes of the user using information associated with the identified set of determined driver gaze directions.

* * * * *